United States Patent [19]
Sood et al.

[11] Patent Number: 5,595,878
[45] Date of Patent: Jan. 21, 1997

[54] DETECTION OF BIOPOLYMERS AND BIOOLIGOMERS WITH BORON HYDRIDE LABELS

[75] Inventors: Anup Sood, Durham; Bernard F. Spielvogel, Cary, both of N.C.

[73] Assignee: Boron Biologicals, Inc., Raleigh, N.C.

[21] Appl. No.: 460,055

[22] Filed: Jun. 2, 1995

[51] Int. Cl.$^6$ ............................ C12Q 1/68; A01N 55/08
[52] U.S. Cl. .................................................. 435/6; 514/64
[58] Field of Search ...................... 435/6, 91.2; 514/64

[56] References Cited

U.S. PATENT DOCUMENTS

| | | | |
|---|---|---|---|
| 3,937,857 | 2/1976 | Brummett et al. | 427/98 |
| 4,046,569 | 9/1977 | Gysling et al. | 96/48 |
| 4,405,720 | 9/1983 | Merril | 436/86 |
| 4,468,466 | 8/1984 | Morrisesy | 436/86 |
| 4,552,848 | 11/1985 | Yudelson et al. | 436/86 |
| 4,554,254 | 11/1985 | Krystal | 436/86 |
| 4,555,490 | 11/1985 | Merril | 436/86 |
| 4,575,452 | 3/1986 | Lee et al. | 422/61 |
| 4,582,808 | 4/1986 | Oosawa et al. | 436/86 |
| 4,672,043 | 6/1987 | Yudelson | 436/86 |
| 4,687,736 | 8/1987 | Newman et al. | 435/7 |
| 4,690,901 | 9/1987 | Giammara et al. | 436/86 |
| 4,703,016 | 10/1987 | Merril | 436/86 |
| 4,782,027 | 11/1988 | Lee et al. | 436/86 |
| 4,812,412 | 3/1989 | Turner | 436/15 |
| 5,023,513 | 6/1991 | Spielvogel et al. | 514/64 |
| 5,064,768 | 11/1991 | Ebata et al. | 436/164 |
| 5,116,734 | 5/1992 | Higgs et al. | 435/28 |
| 5,130,302 | 7/1992 | Spielvogel et al. | 514/45 |
| 5,143,907 | 9/1992 | Spielvogel et al. | 514/64 |
| 5,177,198 | 1/1993 | Spielvogel et al. | 536/25.33 |
| 5,192,688 | 3/1993 | Switzer, III et al. | 436/63 |
| 5,206,122 | 4/1993 | Noppe et al. | 430/414 |
| 5,254,706 | 10/1993 | Spielvogel et al. | 556/402 |
| 5,256,394 | 10/1993 | Spielvogel | 424/5 |
| 5,260,427 | 11/1993 | Spielvogel et al. | 536/17.1 |
| 5,280,119 | 1/1994 | Spielvogel et al. | 544/229 |
| 5,286,853 | 2/1994 | Spielvogel et al. | 534/16 |
| 5,292,873 | 3/1994 | Rokita et al. | 536/24.3 |
| 5,294,370 | 3/1994 | Wichers et al. | 252/313.1 |
| 5,312,816 | 5/1994 | Spielvogel et al. | 514/64 |

FOREIGN PATENT DOCUMENTS

| | | |
|---|---|---|
| 0369546 | 5/1990 | European Pat. Off. . |
| 0370561 | 6/1992 | European Pat. Off. . |

OTHER PUBLICATIONS

Tjarks et al., "Advances in Neutron Capture Therapy", Soloway et al. eds., Plenum Press, NY pp. 289–292 (1993).
Novick et al., "Advances in Neutron Cap[ture Therapy", Soloway et al. eds., Plenum Press, NY pp. 357–360 (1993).
Yanagie et al., "Advances in Neutron Therapy", Soloway et al. eds., Plenum Press, NY pp. 367–370 (1993).
Porter, K., et al., One–Step PCR Sequencing. Poster presented at Genome Sequencing and Analysis Conference V, Oct. 23–27, 1993. Abstract published in Genome Science and Technology, J. C. Venter, ed., Mary Ann Liebert, Inc., p. 55, Abs. C19 (1993).
Tomasz, J., et al., 5'–P–Borane–Substituted Thymidine Monophosphate and Triphosphate. Angewandte Chemie 31, 1373–1375 (1992).
Spielvogel, B. F. et al., Boron Containing Nucleic Acids. Progress in Neuron Capture Therapy for Cancer, B. J. Allen et al., ed., Plenum Press, N.Y. 211–213 (1992).
Sood, A., et al., Boron Containing Nucleic Acids. Synthesis of Oligodeoxynucleoside Boranophosphates. Journal of the American Chemical Society 112, 9000–9001 (1990).
Spielvogel, B. F., et al., From boron analogues of amino acids to boronated DNA: potential new pharmaceuticals and neutron capture agents. Pure & Appl. Chem., 63, 415–418 (1991).
Okuno Pharm Ind KK; (Surt–) Surtech Kariya KK, Electroless nickel @–boron plating– using soln, contg. nickel sulphate, chelating agent, boron contg. reducing agent, dithioethanol and thiodiglycolic acid. A Derwent WPI title for Japanese Patent, JP 6192846 (1994).
Wellum, G. R. et al., Complementary Thin–Layer Chromatographic Separations of Some Polyhedral Borane Anions And Their Derivatives. Journal of Chromatography, 103, 153–159 (1975).

*Primary Examiner*—Stephanie W. Zitomer
*Assistant Examiner*—Ethan C. Whisenant
*Attorney, Agent, or Firm*—Elman & Associates

[57] ABSTRACT

A method is disclosed for detecting boron labeled biopolymers, biooligomers, and other species that bind to the biopolymers, and biooligomers with specificity. The biopolymers include RNA, DNA and proteins. The biooligomers include RNA oligomers, DNA oligomers, and peptides. The biopolymers and biooligomers are labeled with a borane, or a boron-hydride moiety. The borane and boronhydride moiety are employed to reduce a metal ion, e.g. silver, to metal or metal oxide, metal boride or other metal species, or alternatively to reduce a dye, or another organic or inorganic compound. The product of the reduction reaction can be visualized with or without signal augmentation, by one or more means, including the naked eye or a microscope, or can be detected through the use of analytical equipment that can detect conductivity, voltage, density, ultraviolet or visible light, fluorescence, luminescence, phosphorescence, paramagnetism, magnetic susceptibility, or any other detectable physical property. The invention provides methods for selectively detecting biopolymers and biooligomers that contain such a boron-label, thereby permitting their selective identification within an environment where unlabeled like and/or unlike species are present.

45 Claims, 5 Drawing Sheets

DETECTION OF BIOPOLYMERS AND BIOOLIGOMERS WITH BORON HYDRIDE LABELS

FIELD OF THE INVENTION

The present invention relates to a method for the detection of polymers and oligomers, especially biopolymers and biooligomers such as DNA or RNA polymers, peptides and proteins. The method uses a novel label comprising a boron-hydrogen moiety to initiate the formation of a detectable signal that permits detection of the desired polymer or oligomer.

BACKGROUND OF THE INVENTION

This invention concerns a new way to label and detect biopolymers for general diagnostic purposes, nucleic acid sequencing and routine molecular biological research. The labeling and detecting method of this invention has a use in such projects as the Human Genome Project.

Labeling of Biopolymers

In recent years, nonradioactive labeling has been the major focus of development for the detection of nucleic acids. The use of radioisotopes, which are still used extensively, suffers from a number of problems which are outlined below. In order to avoid these problems, several non-radioactive methods have been developed for use in select applications. A brief description of major labeling methods and their shortcomings is given below.

Radioisotope Labeling

Several radioisotopes like $^3H$, $^{14}C$, $^{35}S$ or $^{125}I$ have been used for labeling nucleic acids. The choice of label depends on a number of factors including desirable detection limits, resolution, etc. for a particular use. For example, the $^{32}P$ label has a very low detection limit, generally 0.02–0.1 pg of probe/cm$^2$ as compared to $^3H$ label with a detection limit of 40–200 pg/cm$^2$ (Tijssen, "Hybridization with Nucleic Acid Probes," Van der Vliet, ed., Elsevier, New York City (1993), p.279). The $^3H$ label, on the other hand, produces a very weak β-radiation suitable for the production of a high resolution image. All of these labels can be readily incorporated mostly by enzymatic incorporation of labeled dNTP's. Radioactive labels do not have any significant effect on hybridization, but can require very expensive equipment for detection.

However, there are two major drawbacks in the use of radiolabels. The first pertains to their instability. Radiolabels have specific half-lives (14 days for $^{32}P$; 12 years for $^3H$). Also, the radiation generated can and does cleave biological molecules, shortening their life considerably. Therefore, a significant drawback to radiolabeled probes is that they cannot be stored in large quantities. This increases their cost.

The second drawback concerns the health hazards associated with radiolabels. Due to radiation hazards, extra handling precautions as well as special disposal methods are required for radiolabels, adding to their cost. These factors have made the use of non-radioactive probes highly desirable. In fact, upcoming changes in Nuclear Regulatory Commission regulations, increases in licensing fees, and the actual limiting of the use of radioactive materials, e.g. in California, have made it necessary to develop detection methods that do not involve the use of radioactivity.

Non-radioisotopic Labeling

There are four major types of non-radioisotope labels that are currently being used for labeling DNA in different applications: i) Bio- and Chemiluminescent labels, ii) Colorimetric detection, iii) Fluorescent labels, and iv) Electron-dense labels.

Chemiluminescence

Chemiluminescence is the emission of light that occurs from certain chemical reactions upon decay of chemi-excited molecules to their ground state. Similar reactions occur in nature where an enzymatic reaction activates the molecule to emit light (bioluminescence). Detection systems that use chemiluminescent labels are highly sensitive, even more sensitive than radiolabel based systems. However, when used as molecular biological probes the sensitivity of these systems depends on several factors including: type of experiment (blot analysis or in situ); type of labeling (direct vs. indirect); signal generation (antibody vs. enzymatic) and the method used to label the probe (random priming, nick translation or PCR). However, luminescent labels are versatile and can be used in a number of diagnostic assays.

Most of the chemiluminescent as well as bioluminescent methods are based on enzymatic activation of the luminescent substrate to produce light. Therefore it is extremely important that samples and reagents be free of endogenous or extraneous enzyme contaminations. Furthermore, probes directly labeled with enzymes can be difficult to use under conditions with high stringency requirements, due to the likelihood of denaturing the enzyme. The other problem with chemiluminescent probes is that the light produced is short-lived: after 15–20 minutes it decays, with a half life of ~1 hour. Therefore, the image has to be stored on a photographic film when a permanent record is desired, adding considerable cost to the assay. In addition, bioluminescent probes require the use of a costly luminometer.

Colorimetry

Colorimetry is the major detection system currently being employed in various nucleic acid probe kits. Although colorimetric based systems are less sensitive than both chemiluminescent and radiolabel based systems, their widespread use may be attributed to the number of substrates available for producing the color. Colorimetry is commonly used to measure the products resulting from the action of peroxidases and phosphatases.

Two types of product are generated by peroxidases on various substrates: those that are soluble in water and those that are not. Examples of substrates producing water soluble products are 2,2'-azinobis(3-ethylbenzthiazoline-6-sulfonic acid), "ABTS," o-phenylenediamine, "OPD," and 3,3',5,5'-tetramethylbenzidine, "TMB." The first two have the disadvantage of being light-sensitive, whereas the TMB reaction gives a high background signal.

The preferred substrates are those that produce water-insoluble products, e.g., 3-amino-9-ethylcarbazole, "AEC," 3,3'-diaminobenzidine, and 4-chloro-1-naphthol. The products generated by AEC and 4-chloro-1-naphthol are soluble in organic solvents which can cause problems in fixing. DAB is relatively sensitive, but its reaction is difficult to control, which creates background problems. The two major problems with colorimetric dyes is that they have a very high toxicity and their color fades over time.

Fluorescence

Current techniques that use fluorescence for detection are plagued by a high and variable background due to the fluorescence of the biological sample itself. This problem is being addressed by the use of time-resolved fluorometry and fluorescent labels with long decay times. This method also provides multiplex capability which makes this technique quite attractive. The problems in using fluorescence are the expensive equipment required, difficulties in quantification, and the need for highly skilled personnel. The Europium-labeled probes currently used for time resolved fluorescence, "TRF" spectrometry, are not suitable for in situ hybridization. TRF assays also require special equipment. Additionally, certain additives used to accelerate hybridization, such as polyethylene glycol, cause high background in TRF assays (Tijssen, op. cit., p. 297).

Gold or Silver staining

Metals with high electron density may be used to label biopolymers. Gold labeling is a method which has been used to stain DNA in the cell. Although not very sensitive by itself, the sensitivity of this technique can be improved by further deposition of silver on the gold particles using silver staining.

The main problem with this technique is that the gold particles are not covalently bound to the probe and can become dissociated during washing. Current attempts to attach large gold complexes to the probes, which can then be reduced to colloidal gold, add considerable cost to the technique.

A colloidal-gold-labeled anti-digoxigenin for detection of digoxigenin-labeled DNA probes is commercially available. The gold particles are physically adsorbed to the anti-digoxigenin and therefore may come off in the cell. Additionally, as in most other methods, the procedure requires modification of both the DNA probes and the anti-digoxigenin.

The silver staining method, which has been used for over a decade for staining proteins, has been recently introduced commercially for the staining of DNA. The greatest advantage of this method over other methods is its simplicity and low cost. Other advantages of this method include that a permanent record is obtained on the gel which can then be stored, and the excess $AgNO_3$ can be precipitated as $AgCl$ and recycled, which minimizes waste. This method is more sensitive than that of ethidium bromide staining, but the sensitivity is lower than methods using chemiluminescent, radiolabeled or fluorescent probes.

For many applications, sensitivity is not a major problem. For example, various DNA amplification techniques are available. However, a significant disadvantage of the original silver staining method is that it is non-specific, i.e., it stains all DNA. Therefore it is not useful as a labeling method for hybridization probes. This precludes its usefulness in many DNA diagnostic methods, though a minor use may exist for sequencing DNA.

Electrochemiluminescence

Electrochemiluminescence is another way of generating luminescence. Electrochemiluminescence has the advantages and disadvantages of other luminescence methods, with an additional disadvantage of requiring specialized equipment. On the other hand, it does not require an enzymatic reaction to produce the luminescence.

Other methods

Another technique that uses non-radioactive isotopes, that is reportedly in development, is Laser Atomization Resonance Ionization Spectroscopy (LARIS). The LARIS technique will be able to localize and quantify isotopes in DNA. It can be used with a number of elements including boron. However, this technique requires very expensive equipment not currently available on the market. Also highly qualified personnel and frequent calibration of the instrumentation is required to achieve good results. Other techniques also are being developed for DNA sequencing, e.g. Sputter Initiated Resonance, Ionization Spectroscopy, time-of-flight mass-spectrometric methods, etc. All of these techniques are too expensive for routine diagnostic use.

Thus, each of the current methods of nucleotide detection has its own drawbacks. An optimal staining method would use substrates and/or products that are not hazardous. Furthermore, this method would provide a permanent record, such as one that involves the reduction of silver salts, which provides totally insoluble deposits. Finally the method would not be dependent on enzymatic reactions, it would be simple, less costly, less time consuming, and more easily automated. The present invention provides such a method. It is a novel, inexpensive and safe method for selectively detecting biopolymers and biooligomers.

PCR Sequencing

The original PCR sequencing method (Scheme 1) involves two major processes separated by a time consuming purification step. The first process is the PCR amplification of the target sequence using normal nucleoside triphosphates, followed by a purification step which involves removal of PCR primers and nucleoside phosphates. This is then followed by a sequencing step that uses dideoxynucleoside triphosphates as chain terminators to provide a sequence "ladder" as described originally by Sanger et al., Proc. Natl. Acad. Sci. 74: 5463 (1977).

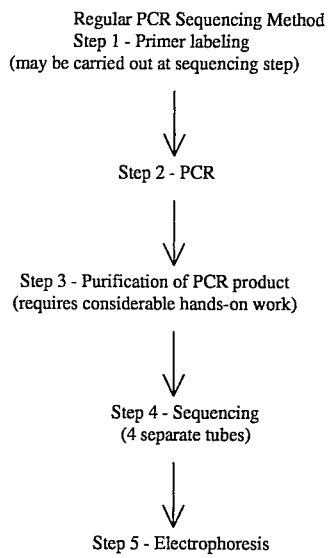

Scheme 1

Regular PCR Sequencing Method
Step 1 - Primer labeling
(may be carried out at sequencing step)

Step 2 - PCR

Step 3 - Purification of PCR product
(requires considerable hands-on work)

Step 4 - Sequencing
(4 separate tubes)

Step 5 - Electrophoresis

Commercial Sequencing Systems

Mauer et. al., *Abstract, Science Innovation '93 Conference*, Aug. 6–10 (1993), Boston Mass., investigated the use of Sequitherm DNA polymerase to sequence unpurified PCR products using cycle sequencing. Although this method eliminates the purification step, the high background makes it difficult to read the gel. This technology is being marketed by Epicentre Technologies.

Amersham Corp. has introduced a PCR product DNA sequencing kit where the purification step has been "simplified" by addition of two enzymatic steps using Exonuclease I to cleave the single-stranded DNA primers and alkaline phosphatase to remove nucleoside triphosphates.

Although it has the potential to allow automation of the whole process, it still requires several steps and requires two additional enzymes.

Other Approaches to Sequencing

Nakamaye et al., *Nucleic Acids Research* (1988), 16, 9947, have published a "direct" sequencing method for the sequencing of PCR-amplified DNA fragments through incorporation of nucleoside-α-thiotriphosphates during PCR followed by cleavage of the phosphorothioate linkage with 2-iodoethanol or 2,3-epoxy-1-propanol. The authors state that their attempts to directly sequence the phosphorothioate-containing DNA after PCR amplification were only moderately successful due to the presence of a high background. In order to decrease the background, they had to gel-purify the PCR product.

These investigators identified other complications. For example, the cleavage of the phosphorothioate group proved to be a minor reaction, yielding a low signal intensity. Furthermore, the cleavage proceeded through two separate pathways, producing a set of four fragments for each phosphorothioate bond cleaved. This led to a doubling of the bands. The doubling makes it even more difficult to read the gel. Nucleoside-α-thiotriphosphates have also been used for sequencing, using the Klenow fragment as the polymerase, followed by digestion with Exonuclease III. Labeit et al., *Methods in Enzymology* (1987), 155, 166. Their use in PCR sequencing, however, has been unsuccessful because it results in uneven band intensities on the gel.

Other approaches include sequencing of PCR products by the Maxam-Gilbert method, Tahara et al., in "The PCR Technique: DNA Sequencing," J. Ellingboe; U. B. Gyllensten, eds., Eaton Publishing Company, Natick, Mass. (1992), p.27. Although this technique eliminates the use of dideoxynucleoside triphosphates, it still requires extensive purification of PCR products prior to sequencing. It also replaces the dideoxynucleoside sequencing step with the chemically induced cleavage steps of Maxam Gilbert sequencing.

Another method involves HPLC purification of PCR products, Warren et al., in "The PCR Technique: DNA Sequencing," op. cit., p.161. Purification using Centricon filters, also have been reported, Mihovilovic et al., *Biotechniques* (1989), 7, 14. However, both these methods still include purification steps and require a second set of nucleotides for sequencing. In addition, use of Centricon filters are not only expensive, but often lead to loss of DNA due to binding to the filter.

Meltzar et. al., in "The PCR Technique: DNA Sequencing," op. cit., p.43, have reported direct sequencing of unpurified PCR product by reducing the amount of primers and dNTP's. However, this lowers the amount of PCR product.

All of the above techniques use the labeling procedures previously outlined.

BRIEF DESCRIPTION

Simplified PCR Sequencing Using Boronated dNTP's

We have recently described an approach based on a method similar to α-thiotriphosphates utilizing nucleoside-α-boranotriphosphates. Tomasz et al. (1992), *Angew. Chem. Int. Ed. Engl.* 31, 1373–1375; Porter et al., Abstracts Genome Sequencing and Analysis Conference V, Oct. 23–27 (1993), Hilton Head Island, S.C., published in *Genome Science and Technology*, Venter, ed., Mary Ann Liebert, Inc., New York City (1993), p.55, Abs. C19. These boronated nucleotides are substrates for a number of polymerases including Klenow, Taq, and vent and can be used in PCR amplification. The rate of incorporation of boronated nucleotides appears to be similar in magnitude to that of normal nucleotides. This allows for a simultaneous incorporation of both the normal and the boronated nucleoside triphosphates via PCR. An extremely important second property of the proposed PCR sequencing method is the nuclease-resistance of the boranophosphodiester backbone that is produced upon incorporation of nucleoside-α-boranophosphates into oligonucleotides. Sood et al., *J. Amer. Chem. Soc.* (1990), 112, 9000.

This simplified PCR sequencing method consists of two main steps: (i) PCR; and (ii) exonuclease cleavage of the PCR products that terminates at a nucleoside-α-boranomonophosphate. This process yields the set of DNA oligomers required for sequencing.

The overall result of this PCR sequencing method using nucleoside-α-boranotriphosphates is a simple four-step process outlined in Scheme 2. The PCR and the exonuclease digestion can be carried out in the same tube, and the whole process of PCR sequencing can be automated. Thus the laborious purification step and the cycle-sequencing step in the methods available today have been substituted by a simple Exo-III digestion step.

Scheme 2

Simplified PCR Sequencing Method
Step 1 - Primer labeling

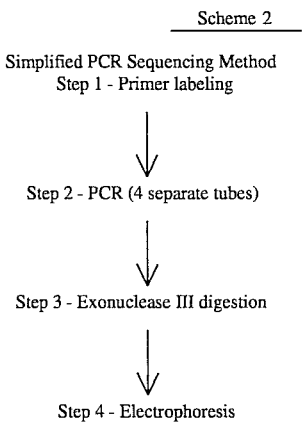

Step 2 - PCR (4 separate tubes)

Step 3 - Exonuclease III digestion

Step 4 - Electrophoresis

One aspect of the present invention describes a unique, facile and specific way to detect the family of oligomers formed by the method described in Scheme 2. Each of the publication and patent references cited in this patent specification is hereby incorporated by reference.

DEFINITIONS

The description of the present invention is facilitated by the use of the following terms which are used in this patent specification and the claims as defined herein:

An "organic molecule" is a compound comprising one or more carbon atoms.

A "small organic molecule" is an organic molecule with a formula weight of less than 2000 grams/mol.

A "nucleotide" is a small organic molecule composed of an N-glycoside of a heterocyclic base, in which the glycoside is also in an ester linkage with a phosphate. The term as used herein also includes modifications and derivatives thereof. Two nucleotides may be connected via a "phosphate linkage."

An "RNA nucleotide" is a nucleotide, wherein the sugar moiety of the glycoside in the nucleotide is ribose.

A "DNA nucleotide" is a nucleotide, wherein the sugar moiety of the glycoside in the nucleotide is deoxyribose.

A "bioorganic polymer" is a polymer comprising nucleotides, amino acids, sugars, or combinations thereof.

A "biooligomer" is a bioorganic polymer comprising at least two but not more than 50 nucleotides, amino acids, sugars, or combinations thereof.

A "biopolymer" is an bioorganic polymer comprising 51 or more nucleotides, amino acids, sugars, or combinations thereof.

A "peptide" is a biooligomer comprising two but not more than 50 amino acids.

A "protein" is a biopolymer comprising 51 or more amino acids.

An "RNA oligomer" is a biooligomer comprising at least two but not more than 50 RNA nucleotides.

A "DNA oligomer" is a biooligomer comprising at least two but not more than 50 DNA nucleotides.

An "RNA polymer" is a biopolymer comprising 51 or more RNA nucleotides.

A "DNA polymer" is a biopolymer comprising 51 or more DNA nucleotides.

"Complementary" means a nucleotide sequence capable of hybridizing to a second such sequence by means of hydrogen bonds established through Watson/Crick, or similar, pairing.

A "ligand" is an organic or inorganic molecule, including but not limited to heteronuclear molecules, halides, lipids, sugars, nucleotides, amino acids, and peptides that binds, with selective affinity, to a ligand receptor.

A "ligand receptor" is an organic or inorganic molecule or polymer including but not limited to metals, biopolymers, and biooligomers, which bind with selective affinity to a ligand.

A ligand has "selective affinity" for specific ligand receptors when the ligand can distinguish the ligand receptors from at least one other ligand receptor under a defined set of reaction conditions. In the most preferred embodiment, the ligand is able to distinguish the specific ligand receptor from all other ligand receptors. Examples of ligands and ligand receptors include but are not limited to: GTP and GTP binding proteins; α-D-mannose and concanavalin A; biotin and avidin; and a virus and an antibody to that virus.

A ligand receptor has "selective affinity" for specific ligands when the ligand receptor can distinguish the ligand from at least one other ligand under a defined set of reaction conditions.

"Target molecule" is the generic term for molecules that are selected to be detected, such as ligands, ligand receptors, biooligomers and biopolymers.

A "boron-label" is a borane, or boron hydride moiety. The borane or boron hydride moiety can reduce a "detection agent," either an organic or inorganic electron acceptor, resulting in the formation of one or more detectable products.

A "detection agent" can be reduced by a boron-label to form a detectable product. Detection agents are either organic or inorganic electron acceptors such as metal cations in metal salts or metal complexes, or organic dyes, like copper leucophthalocyanine and nickel leucophthalocyanine.

A "detectable product" is a product of the reaction of a boron-marker, defined below, with a detection agent that alone or through an additional chemical development step produces (and/or augments) a signal that can be detected by one or more means including but not limited to visual detection, or analytical equipment that can detect conductivity, density, ultraviolet or visible light, fluorescence, luminescence, phosphorescence, paramagnetism, nuclear magnetic resonance, or magnetic susceptibility.

A "signal" is that property produced by the detectable product that is detectable.

A "signal produced by a detectable product" includes all properties that make that detectable product detectable by visual detection and/or with the aid of analytical equipment.

A "nucleation site" is the site where further development of the signal occurs as the result of the interaction between a nucleation agent and a detection agent. The term nucleation site includes the nucleation agent that catalyses this further development of the signal. An example of a nucleation agent is the detectable product formed from the reduction of a metal salt or metal complex by a boron-label.

"Visual detection" includes detecting a signal with the naked eye or in conjunction with visual aids including but not limited to prescription glasses, magnifying glasses and microscopes.

"Analytical equipment" includes, but is not limited to, instruments capable of detecting conductivity, voltage, density, ultraviolet or visible light, fluorescence, luminescence, phosphorescence, paramagnetism, nuclear magnetic resonance, and magnetic susceptibility.

A "boron-building-block" is a small organic molecule that comprises one or more boron-labels, including but not limited to sugars, nucleotides, and amino acids, which can serve as the repeat units of a biopolymer or a biooligomer.

A "labeled probe" is a biopolymer, biooligomer, ligand receptor, or ligand, that comprises at least one "boron-label" and has a selective affinity to associate with a target molecule such that, when associated with the appropriate target molecule, the target molecule can be detected.

A labeled probe has "selective affinity" for specific target molecules when the labeled probe can distinguish the target molecules from at least one non-target molecule under a defined set of reaction conditions. In the most preferred embodiment, the labeled probe molecule is able to distinguish the target molecules from all non-target molecules.

A "boron-marker" is a boron-label, a boron-building-block, and/or a labeled probe that is capable of being associated with a target molecule.

An "associated boron-marker" is a boron-marker bound to a target molecule by means including but not limited to covalent bonds, and/or hydrogen bonds, and/or ionic interactions, and/or hydrophobic interactions, and/or charge-transfer complexation, and/or metal to ligand coordination bonds.

An "unassociated boron-marker" is a boron-marker that is not associated with a target molecule.

"Eliminating unassociated boron-marker" includes but is not limited to: (1) depleting the unassociated boron-marker by selectively oxidizing the boron-label comprised by the boron-marker, and/or (2) physically removing the unassociated boron-marker.

"Eliminating unhybridized labeled probe" includes but is not limited to: (1) depleting the unhybridized labeled probe by selectively oxidizing the boron-label comprised by the labeled probe, and/or (2) physically removing the unhybridized labeled probe.

A "preliminary oxidizing agent" is an oxidizing agent that when added to a mixture of associated boron-marker and unassociated boron-marker, selectively oxidizes the boron-label comprised by the unassociated boron-marker.

"B-H" moiety is a borane, or boron hydride moiety.

"Polymerase chain reaction" ("PCR") refers to a process for amplifying nucleic acid sequences as described in U.S. Pat. Nos. 4,683,202 and 4,683,195, or any equivalent procedure including procedures using alternative polymerases to the Taq polymerase.

"Strand displacement amplification" ("SDA") is an isothermal in vitro DNA amplification technique as described in GT Walker, *PCR Methods Appl.*, 3(1), 1 (1993) and GT Walker et al., *Nucleic Acids Res*, 20(7), 1691 (1992).

"Self-sustained sequences replication" ("3SR") refers to a process for amplifying nucleic acid sequences using oligonucleotide primers, a reverse transcriptase, DNA-dependent RNA polymerase, and RNase H as described in J. C. Guatelli et al., *Proc. Natl. Acad. Sci.* USA, 87, 1874 (1990).

"Replication using Qβ replicase" refers to a process for amplifying and/or detecting nucleic acid sequences that uses RNA bacteriophage Qβ replicase to effect amplification as described in P. M. Lizardi et al., *Bio/Technology*, 6, 1197 (1988).

"Ligase chain reaction" ("LCR"), refers to a process for amplifying nucleic acid sequences that uses a DNA ligase to join oligonucleotides that bind to a target as described in K. J. Barringer et al., *Gene*, 89, 117 (1990) and D. Y. Wu and R. B. Wallace, *Genomics*, 4, 560 (1989).

Transcription based amplification refers to a process for amplifying nucleic acid sequences that uses oligonucleotide primers, a reverse transcriptase, and DNA-dependent RNA polymerase as described in D. Y. Kwoh et al., *Proc. Nat'l Acad. Sci.* USA, 86, 1173 (1989).

"Standard nucleoside triphosphates" are nucleoside triphosphates that do not contain a —$BH_3$ moiety in place of a non-bridging oxygen.

"Adenosine 5'-α-boranotriphosphate" is a modified adenosine triphosphate, having a —$BH_3$ moiety in place of a non-bridging oxygen at the α-phosphorous. The —$BH_3$ serves as the boron-label.

"Deoxyadenosine 5'-α-boranotriphosphate" is a modified deoxyadenosine triphosphate, having a —$BH_3$ moiety in place of a non-bridging oxygen at the α-phosphorous. The —$BH_3$ serves as the boron-label.

"Uridine 5'-α-boranotriphosphate" is a modified uridine triphosphate, having a —$BH_3$ moiety in place of a non-bridging oxygen at the α-phosphorous. The —$BH_3$ serves as the boron-label.

"Thymidine 5'-α-boranotriphosphate" is a modified thymidine triphosphate, having a —$BH_3$ moiety in place of a non-bridging oxygen at the α-phosphorous. The —$BH_3$ serves as the boron-label.

"Cytosine 5'-α-boranotriphosphate" is a modified cytosine triphosphate, having a —$BH_3$ moiety in place of a non-bridging oxygen at the α-phosphorous. The —$BH_3$ serves as the boron-label.

"Deoxycytosine 5'-α-boranotriphosphate" is a modified deoxycytosine triphosphate, having a —$BH_3$ moiety in place of a non-bridging oxygen at the α-phosphorous. The —$BH_3$ serves as the boron-label.

"Guanosine 5'-a-boranotriphosphate" is a modified guanosine triphosphate, having a —$BH_3$ moiety in place of a non-bridging oxygen at the α-phosphorous. The —$BH_3$ serves as the boron-label.

"Deoxyguanosine 5'-α-boranotriphosphate" is a modified deoxyguanosine triphosphate, having a —$BH_3$ moiety in place of a non-bridging oxygen at the α-phosphorous. The —$BH_3$ serves as the boron-label.

A "nucleotide 5'-α-boranotriphosphate" is a nucleoside triphosphate having a —$BH_3$ moiety in place of a non-bridging oxygen. The —$BH_3$ serves as the boron-label. Nucleotide 5'-α-boranotriphosphates include but are not limited to adenosine 5'-α-boranotriphosphate, deoxyadenosine 5'-α-boranotriphosphate, uridine 5'-α-boranotriphosphate, thymidine 5'-α-boranotriphosphate, cytosine 5'-α-boranotriphosphate, deoxycytosine 5'-α-boranotriphosphate, guanosine 5'-α-boranotriphosphate, and deoxyguanosine 5'-α-boranotriphosphate.

A "boranomonophosphate" is a nucleoside monophosphate wherein the phosphate of the nucleotide has a —$BH_3$ moiety in place of a non-bridging oxygen, i.e., a nucleotide 5'-α-boranomonophosphate.

A "boranomonophosphate linkage" is a linkage between two nucleotides wherein the two nucleotides are linked via a phosphate linkage having a —$BH_3$ moiety in place of a non-bridging oxygen.

A "borano-terminated oligomer or polymer" is an oligomer or polymer of an RNA or DNA polymer or oligomer that has been at least partially digested by a nuclease, and wherein the terminal nucleotide linkage of the oligomer or polymer has a —$BH_3$ moiety in place of a non-bridging oxygen.

$C^b$DNA is a DNA oligomer or polymer wherein, every linkage 5' to a cytosine residue is a borano-monophosphate linkage. See FIG. 1.

| | |
|---|---|
| "mg" = milligram, | "ng" = nanogram |
| "ml" = milliliter, | "μl" = microliter |
| "mM" = millimolar, | "μM" = micromolar |
| "TpT" = Thymidylyl (3' → 5') Thymidine | |
| "TpBT" = Thymidylyl (3' → 5') Thymidine Borane phosphonate. | |

Terms used in the claims below, that are defined in the Definitions section of this application are to be read as having the meanings provided in this section.

SUMMARY OF THE INVENTION

The present invention provides a new, general, labeling method for ligands, biopolymers, and biooligomers. The method labels ligands, biooligomers and biopolymers with a powerful reducing boron-hydrogen (B-H) moiety. The B-H, either a borane or a boron hydride species, serves as a label because it reacts with electron-accepting detection agents to form detectable products that allow for detection of the label and, hence, for detection of the ligands, biopolymers, and biooligomers.

The detection agents include but are not limited to organic dyes and metal cations. The metal cations include but are not limited to silver, nickel, copper, palladium, platinum and gold. The product of the reaction between the B-H moiety and a metal cation is either the free metal or the metal boride. Detectable products thus formed may include, but are not limited to, magnetically active metal borides, catalytically active metal borides, and visible precipitates that are selectively deposited at the site of the B-H moiety.

A preferred detection agent is a cation of a heavy metal. Thus, in preferred embodiments of the invention, the reaction of the B-H moiety with a detection agent produces a nickel boride, a copper boride, a molybdenum blue precipitate, or a tungsten blue precipitate. In the most preferred embodiment, the reaction produces detectable metallic silver.

Previous procedures for detecting fragments of DNA by silver staining rely on the pretreatment of the DNA with standard reducing agents such as hydroquinone or formaldehyde to reduce the silver salts to metallic silver. This results in the non-specific staining of the DNA fragments and does not distinguish between different DNA sequences. In comparison to these earlier silver staining methods, the present invention describes a method to selectively stain specific DNA sequences. This is accomplished by placing a reducing agent on a probe that preferentially hybridizes to a specific DNA sequence. The reducing agent of the present invention is, either a borane or a boron hydride species, i.e., a boron-label, that is capable of chemically reducing a detection agent, such as a silver salt, as the initial nucleation of the detection agent. The boron-label can be built into a labeled probe that preferentially hybridizes to a selected DNA sequence. In this manner only the DNA fragments containing the specific sequence that hybridizes with the probe will be stained. A schematic diagram illustrating the difference between the prior techniques and the present invention is shown in FIG. 2.

The present invention employs a principle present in both photographic film development, and in electroless plating. The principle works to selectively deposit large amounts of a metal, e.g. silver, at a catalytic site. The catalytic sites, also called nucleation sites, are generally small metal deposits that are obtained at each particular site by any of a number of the different known techniques including photochemical deposition and thermodecomposition of a selected product at the desired site.

The invention includes a developer solution that contains a second detection agent, a reducing agent, and a stabilizer. The second detection agent is selected from a group including but not limited to a metal complex, a metal salt or an organic dye. The reducing agent is selected from a group including but not limited to formaldehyde, hydroquinones, amine-boranes, phosphine-boranes, phosphite-borane, amino-phenols, hydroxyl phenylglycine and mixtures thereof. The stabilizer is selected from a group including but not limited to gum arabic, Pinacryptol Yellow, sodium sulfite, sodium bisulfite, and sodium citrate. These aspects of the invention can be used in any embodiment of the invention that involves a detection agent that is either a metal salt or a metal complex.

In a preferred embodiment of the present invention, the reducing agent is $BH_3$ and the detection agent is a silver salt or silver complex. The $BH_3$ reduces up to six atoms of silver. These atoms then serve as a catalytic site or nucleation site for small metal deposits that can be detected by visual detection or with the aid of analytical equipment.

This aspect of the invention can include a developer that is stable in the absence of nucleation. The stable developer only deposits silver at the nucleation sites. These nucleation sites will only be generated when reduction with borane or borohydride takes place. Stable developers include a stabilizer such as gum arabic, Pinacryptol Yellow, sodium sulfite, sodium bisulfite, and sodium citrate.

One aspect of this invention uses solid substrates. Solid substrates include but are not limited to membranes, microtiter plate wells, and beads. Membranes are made of materials including but not limited to glass, nylon, nitrocellulose, and polyvinylidene difluoride (Polyvinyldifluoridine). Beads are made of materials including but not limited to, glass, plastic, metal and/or a magnetic material, agarose, dextran, PDX-Cross-linked dextran beads, Sephadex, Sephacryl, Sepharose, Degalan, Superdex, Superose, Trisacryl Plus-Beaded poly(N-tris[hydroxymethyl]methyl methacrylamide) and polystyrene. This aspect of the invention can be used whenever a solid substrate can be used.

The invention includes a unique method of labeling ligands, biooligomers, and biopolymers by coupling them with a reducing agent, which can then react with an appropriate electron acceptor, i.e., a detection agent, to form a detectable product that produces a signal. The signal can be detected by one or more means including but not limited to visual detection or analytical equipment. The detection may require a further signal augmentation step.

Visual detection includes detecting a signal with the naked eye or in conjunction with visual aids including but not limited to prescription glasses, magnifying glasses and microscopes. Analytical equipment includes, but is not limited to, instruments capable of detecting conductivity, voltage, density, ultraviolet or visible light, fluorescence, luminescence, phosphorescence, paramagnetism, nuclear magnetic resonance, and magnetic susceptibility.

The reducing agent, i.e., the boron-label, is a borane, or boron hydride. The labeled species include, but are not limited to DNA oligomers, RNA oligomers, DNA polymers, RNA polymers, peptides, proteins and other biooligomers and biopolymers synthesized from nucleotides, amino acids and other small organic polymerizable compounds.

In one aspect of this invention a boron-label is covalently attached to a target molecule which already has been synthesized. In another aspect of the invention, the boron-label, e.g. a boron building block, is incorporated into the target molecule by adding the boron-label to a compound which is incorporated into the target molecule as it is synthesized. By either method the boron-marker becomes covalently bonded to the target molecule.

Another aspect of this invention includes a method of detecting a specified target molecule using a boron-label as part of a boron-marker. The method includes contacting an unassociated boron-marker with the selected target molecule. Because of the selective affinity of the boron-marker for the target molecule, the boron-marker becomes selectively associated at the site of the target molecule. The remaining unassociated boron-marker is removed or inactivated. A detection agent that can react with the associated boron-marker is added to and incubated with the associated boron-marker so as to allow the boron-marker to chemically reduce the detection agent thereby forming a detectable product that produces a signal. The signal can be detected by one or more means including but not limited to visual detection or analytical equipment. The detection may require a further signal augmentation step. The measured signal thus allows the detection of the specified target molecule.

The invention also comprises various conditions for incubating a boron-marker with a detection agent in order to form a detectable product. These conditions can be used in any embodiment of the invention that involves an associated boron-marker and a detection agent. These conditions can also be used where the boron-marker is employed to chemically reduce the detection agent to a detectable state either with or without subsequent signal augmentation. The pH, temperature, and time for the boron-marker and the detection agent to incubate together can be varied.

The time for which the boron-marker and the detection agent are incubated together may be varied from as little as 5 seconds to as much as 4 hours. Preferably the boron-marker and the detection agent are incubated together for between 1 minute to 30 minutes. Most preferably they are incubated together for 5 to 10 minutes.

The boron-marker and the detection agent may be incubated together between pH 1 and pH 10. In a preferred embodiment they are incubated together between pH 3 and pH 8. In a more preferred embodiment the incubation is peformed between pH 6.8 and pH 7.8. Most preferably they are incubated together at pH 7.4.

The temperature of incubation for the incubation of the boron-marker and the detection agent may be varied between 0° and 80° C. In a preferred embodiment the temperature is between 15° and 30° C. In a more preferred embodiment incubation is at a temperature between 22° and 24° C.

Thus in the most preferred embodiment of the invention, the boron-marker and the detection agent are incubated together for 5 to 10 minutes, at a temperature between 22° and 24° C. and at a pH of 7.4.

In one aspect of the invention the detection agent has an oxidized state and a reduced state, with the oxidized state being reducible to the reduced state by the boron-marker, and the reduced state being both detectable and distinguishable from said oxidized state.

The possible detection agents include but are not limited to organic dyes and metal cations. In one embodiment the detection agent is an organic dye in the oxidized state. In a preferred embodiment, the detection agent is a metal salt or a metal complex, .that upon reduction is either reduced to its metallic state, forms a metal boride, or forms a colored metal oxide. In a more preferred embodiment the metal salt or metal complex is selected from the group consisting of salts or complexes of silver, cadmium, cobalt, copper, gold, iridium, lead, mercury, nickel, palladium, platinum, and rhenium. In the most preferred embodiment the detection agent is a silver salt or silver complex.

One aspect of the invention comprises augmenting the signal due to the detectable product when the detection agent is either a metal salt or a metal complex. The reduced metal salt or complex serves as a nucleation site for the further development of the signal through the reduction of additional detection agent. An alternative aspect of this invention comprises an additional step of adding a second detection agent following the formation of the detectable product. In a more refined form of this aspect of the invention, the remaining unreduced initial detection agent is removed prior to the addition of this second detection agent.

In one embodiment of this aspect of the invention, the detection agent is a silver salt or silver complex. The silver salt or silver complex is reduced to metallic silver by the boron-marker. The metallic silver thus produced serves as a nucleation site for further signal development. For example, the metallic silver can serve as the nucleation site for the deposition of additional silver using chemical reactions such as those performed in photographic image development.

In a preferred embodiment, the detection agent comprises a catalytically active metal having a valence state of +2, such as palladium or platinum, which can be reduced by the associated boron-marker. The resulting reduced metal serves as a nucleation site onto which may be deposited another metal, e.g. copper, cobalt, nickel, silver, or gold, by a technique analogous to electroless plating. The presence of the other metal is then detected. In this embodiment, the catalytically active metal e.g., palladium or platinum, serves as a nucleation site for further signal development. This aspect of the invention can be used in any embodiment of the invention that involves a detection agent comprising a catalytically active metal having a valence state of +2, such as palladium or platinum, which can be reduced by the associated boron-marker.

In another aspect of the invention, the boron-marker associates with the target molecule due to the boron-marker's selective affinity for the target molecule. In one embodiment of this invention, both the target molecule and the boron-marker are biopolymers or biooligomers. In another embodiment of the invention the target molecule is an RNA or DNA polymer and the boron-marker is an RNA or DNA oligomer that is complementary to the target molecule and can hybridize with it. In yet another embodiment, the boron-marker is a ligand receptor, including but not limited to an antibody, a lectin or a receptor protein and the target molecule is a ligand with which these ligand receptors specifically react.

In another embodiment of this invention the boron-marker is a labeled probe. In a preferred embodiment the labeled probe is either a biooligomer or a biopolymer. In a more preferred embodiment the labeled probe is a DNA or RNA oligomer that is complementary to a DNA or RNA target biopolymer. In the most preferred embodiment, the labeled probe is a DNA oligomer that is complementary to a DNA or RNA target biopolymer.

In one embodiment of the invention, the target molecule and the labeled probe are both biopolymers or biooligomers. In another embodiment either the target molecule or the labeled probe is a biopolymer or biooligomer.

In a preferred embodiment either the target molecule or the labeled probe or both are selected from the group consisting of an RNA polymer, an RNA oligomer, a DNA polymer, a DNA oligomer, a protein, and a peptide. In a more preferred embodiment the target molecule is a DNA polymer or a DNA oligomer and the labeled probe is either an RNA oligomer or a DNA oligomer. In the most preferred embodiment the target is a DNA polymer and the labeled probe is an RNA oligomer.

In another embodiment the labeled probe is either a protein or a peptide. In a more preferred embodiment, the labeled probe is a protein that is an antibody specific for a target antigen. In yet another embodiment, the protein is a lectin and the target molecule is a non-reducing sugar moiety. In still another embodiment, the protein is a binding protein and the target molecule is the receptor for that protein. In a more preferred embodiment, the protein is a cytokine and the target molecule is a binding receptor for that cytokine.

This invention provides a method for the separation of the associated boron-marker from the unassociated boron-marker by physical means such as (a) attaching the target molecule to a solid substrate, (b) associating the boron-marker to the target molecule and (c) washing away all unassociated boron-marker.

Another embodiment of this invention uses solid substrates comprising membranes made of materials including but not limited to glass, nylon, nitrocellulose, and polyvinylidene difiuoride (Polyvinyldifiuoridine). In a preferred embodiment the separation entails Southern, northern or western blot analyses. In a most preferred embodiment the separation entails northern or Southern blot analyses.

In an alternative embodiment, the target molecule is attached to a solid substrate such as a microtiter plate well, or a bead. In a preferred embodiment, the solid substrate is a bead of a material including but not limited to, glass, plastic, metal and/or a magnetic material, agarose, dextran, PDX-Cross-linked dextran beads, Sephadex, Sephacryl, Sepharose, Degalan, Superdex, Superose, Trisacryl Plus-Beaded poly(N-tris[hydroxymethyl]methyl methacrylamide) and polystyrene. In a more preferred embodiment, the bead is a magnetic material.

This invention also includes a method of adding a preliminary oxidizing agent that selectively oxidizes the reducing agent of the unassociated boron-marker, prior to the addition of the detection agent. The preliminary oxidizing agent is selected to be incapable of reacting with the boron-marker associated with the target molecule for reasons that include but not limited to the fact that the reaction is sterically hindered, or the reduction potential of the reducing agent is changed upon binding so that it is no longer oxidizable by the preliminary oxidizing agent.

In one form of the invention, the preliminary oxidizing agent is attached to a solid substrate such as a bead, and thereby inaccessible to the reducing agents of the boron-label on the associated boron-markers. In one embodiment of the invention, the solid substrate to which the preliminary oxidizing agent is attached is a bead of a material that may include but is not limited to: glass, plastic, metal and/or a magnetic material, agarose, dextran, PDX-Cross-linked dextran beads, Sephadex, Sephacryl, Sepharose, Degalan, Superdex, Superose, Trisacryl Plus-Beaded poly(N-tris[hydroxymethyl]methyl methacrylamide) and polystyrene. In a preferred embodiment the bead is a magnetic material.

In a more preferred embodiment the method comprises the steps: (a) adding a boron-marker to a solution containing the target molecule; (b) incubating the target molecule with the boron-marker; (c) adding the preliminary oxidizing agent, that is attached to a solid substrate (such as beads) to the solution and oxidizing the unassociated boron-marker; (d) removing the solid substrate from the solution; (e) adding the detection agent to the solution; (f) incubating the detection agent with the associated boron-marker, so as to chemically reduce the detection agent and form a detectable product which produces a signal; and (g) detecting the signal produced by the detectable product by visual detection or with the aid of analytical equipment.

This invention also provides a method of selectively associating a boron-marker with a specific target molecule by incorporating the boron-marker into the specific target molecule. This aspect of the invention uses a process such as the polymerase chain reaction which reaction fails in the absence of the target molecule. Unincorporated boron-marker is eliminated, via its removal or inactivation. A detection agent is then added to the incorporated boron-marker. The incorporated boron-marker and the detection agent are incubated so as to chemically reduce the detection agent and form a detectable product which produces a signal. The signal can be detected by one or more means including but not limited to visual detection or analytical equipment. The detection may require a further signal augmentation step as described above.

In one embodiment, the boron-marker is a boron-building-block. In a preferred embodiment, this boron-building-block comprises an amino acid, that is incorporated into a newly synthesized peptide or protein labeled probe. In a more preferred embodiment, the boron-marker is a nucleotide and the newly synthesized labeled probe is an RNA polymer, RNA oligomer, a DNA oligomer, or a DNA polymer. In the most preferred embodiment, the boron-building-block comprises a DNA nucleotide, and the labeled probe is a newly synthesized DNA oligomer that can be used to hybridize with DNA and RNA oligomers.

In another embodiment, the boron-building-block is a nucleotide and incorporation is achieved using polymerase chain reaction (PCR), in situ PCR, strand displacement amplification (SDA), self-sustained sequence replication (3SR), replication using Qβ replicase, ligase chain reaction (LCR), transcription based amplification or another amplification technique.

In still another embodiment, biooligomers and biopolymers comprising DNA or RNA nucleotides are amplified in the presence of one or more nucleotide 5'-α-boranotriphosphates, by methods including but not limited to polymerase chain reaction (PCR), in situ PCR, strand displacement amplification (SDA), self-sustained sequence replication (3SR), replication using Qβ replicase, ligase chain reaction (LCR), and transcription based amplification.

This invention, provides a staining technique useful in the sequencing of DNA and RNA biopolymers and oligomers. In one embodiment of the invention boron-building-blocks comprising deoxyadenosine, deoxythymidine, deoxycytosine, and deoxyguanosine 5'-α-boranotriphosphates synthesized by the methods described in Tomasz et al. (1992), op. cit., are placed into four separate amplification containers. The four separate amplification reactions are performed in the presence of template, primers and deoxyadenosine triphosphate, deoxythymidine triphosphate, deoxycytosine triphosphate, and deoxyguanosine triphosphate. At the specific site of the boranomonophosphate linkage the phosphodiester backbone of the products of the amplifications is resistant to certain nucleases, e.g., exonuclease III. Therefore, each of the amplification reaction products are digested with an exonuclease to produce oligomers or polymers which terminate at the base-specific deoxynucleoside boranomonophosphate. Porter et al., op. cit. These borano-terminated oligomers or polymers are then separated. A detection agent is added to these oligomers or polymers and, following an incubation period, a detectable product is formed which produces a signal. The signal can be detected by one or more means including but not limited to visual detection or analytical equipment. The detection may require a further signal augmentation step as described above.

The detection agents may be chosen from any of those described above. Similarly the incubation conditions for reacting the detection agents with the borano-terminated oligomers or polymers is the same as for other aspects of the invention.

In a preferred embodiment of the invention the amplifications are performed by PCR amplification and the borano-terminated oligomers or polymers are separated by gel electrophoresis. In this preferred embodiment, the detection agent is a metal salt or a metal complex. In the most preferred embodiment the metal salt or metal complex contains silver, platinum, or palladium.

In one embodiment, the detectable product formed by the reaction of borano-terminated oligomers or polymers with the metal salt or metal complex produces a signal that can be detected by visual detection. In a more preferred embodiment the signal from the detectable product is detected by analytical equipment. In the most preferred embodiment, the signal from the detectable product is detected by a densitometer.

One embodiment of this invention is a method of detecting a target molecule comprising nucleotides, i.e., an RNA or DNA oligomer or polymer. The target molecule is first associated with a labeled probe. Unassociated labeled probe is then eliminated by means including but not limited to depleting the unassociated labeled probe by selectively oxidizing the boron-label comprised by the labeled probe and/or by physically removing the unassociated labeled probe. A detection agent comprising either a soluble silver salt or a soluble silver complex is then added to the associated labeled probe. The associated labeled probe and the detection agent are incubated under conditions and for a time sufficient to chemically reduce the silver to its metallic state. The metallic silver produced serves as a nucleation site for development by a silver developer, added to facilitate the deposit of additional silver. The deposition of the additional silver is achieved using chemical reactions similar to those performed in photographic image development. The metallic silver can then be detected by the methods described above.

In a more preferred embodiment of the invention, the excess detection agent remaining following the reduction of the detection agent by the boron-label contained by the labeled probe during the incubation step, is removed prior to the signal augmentation step.

In another embodiment, the labeled probe is either an RNA or DNA oligomer or polymer. The nucleotides incorporated into the labeled probe are either only nucleotide 5'-α-boranotriphosphates, or a mixture of nucleotide 5'-α-boranotriphosphates with standard nucleoside triphosphates. The labeled probe is amplified by a process such as polymerase chain reaction (PCR), in situ PCR, strand displacement amplification (SDA), self-sustained sequences replication (3SR), replication using Qβ replicase, ligase chain reaction (LCR), and transcription-based amplification. The amplified labeled probe comprising a boranomonophosphate linkage is then associated with target DNA or RNA oligomers or polymers, which have been attached to a solid support, and are complementary to the labeled probe. The solid support is selected from a group such as a bead, a membrane or a microtiter plate. Unassociated and target molecules, are eliminated by washing them away from the solid support. Unassociated nucleotides and labeled probe are washed away and a detection agent, either a metal salt or a metal complex, is added to the solid support. The detection agent and the associated labeled probe are incubated. They then form a detectable product which produces a signal. The product produced can serve as a nucleation site for further signal development. Unreacted detection agent is eliminated by washing with aqueous solution.

If the signal is augmented using a developer solution the developer solution contains a second detection agent, a reducing agent, and a stabilizer. The second detection agent may be, e.g. a metal complex, a metal salt or an organic dye. The unreacted developer is then eliminated. The unreacted developer is eliminated by washing with an aqueous solution.

The augmented signal can be detected by one or more means including but not limited to visual detection or analytical equipment. In a preferred embodiment, the developer is stable in the absence of a nucleation site.

Pre-amplification of Target

This invention also includes a specific method for determining whether a target molecule comprising a nucleic acid is contained in a sample. The sample is treated as if the target molecule is present in the sample. If the target molecule is present in the sample, it is amplified in the presence of a primer containing a covalently linked ligand. The nucleotides incorporated into the target molecule are RNA nucleotides or DNA nucleotides but are not 5'-α-boranotriphosphates. The amplification produces a target population comprising DNA polymers, DNA oligomers, RNA polymers, and/or RNA oligomers covalently linked to the ligand. Amplification is achieved by a process such as polymerase chain reaction (PCR), in situ PCR, strand displacement amplification (SDA), self-sustained sequences replication (3SR), replication using Qβ replicase, ligase chain reaction (LCR), and transcription-based amplification.

After the target molecule is amplified, it is associated with a ligand receptor that has a selective affinity for the ligand covalently linked to the target molecule. The ligand receptor is attached to a solid substrate. The ligand of the target molecule associates with the ligand receptor forming a ligand-ligand receptor complex that is attached to the solid substrate. The unassociated nucleotides and unassociated target molecules are eliminated by washing them from the solid substrate. A labeled probe that is complementary to the target molecule is then added to the target molecule. The labeled probe may be a DNA oligomer, an RNA oligomer, a DNA polymer, or an RNA polymer. The labeled probe hybridizes to the target molecule, and the unhybridized labeled probe is eliminated. A detection agent is then added to the hybridized labeled probe. The detection agent is incubated with the hybridized labeled probe so as to chemically reduce the detection agent and form a detectable product, which produces a signal. The signal can be detected by one or more means including but not limited to visual detection or analytical equipment. The detection may require a further signal augmentation step as described above. Detection of the signal indicates that the target molecule is contained in the sample.

In a preferred embodiment the covalently coupled ligand is biotin and the ligand receptor is avidin or streptavidin. The detection agent is a metal salt or metal complex. In another further embodiment the detection agent is a metal salt or metal complex, and the detectable product serves as a nucleation site for further signal development. First, the unreduced detection agent is eliminated by washing it away from the solid substrate. Next, the signal due to the detectable product is augmented using a developer solution. The unreacted developer solution is then eliminated by washing, and the augmented signal is detected.

In a more preferred embodiment the developer solution comprises a second detection agent, a reducing agent, and a stabilizer. In another more preferred embodiment, the second detection agent is a metal complex, a metal salt or an organic dye, and the developer is stable in the absence of nucleation. In the most preferred embodiment the ligand is biotin, and the ligand receptor is either streptavidin or avidin. Biotin may be incorporated into the target molecule using commercially available reagents such as Biotin-ON Phosphoramidite, for example, produced by Clontech Laboratories, Inc., Palo Alto, Calif. with or without Clonetech's Biotin-21-dUTP Nick Translation Labeling Kit.

Kit Embodiments of the Invention

The instant invention may also be provided in the form of a kit. Such kits contain, but are not limited to, the following items: nucleotides, biooligomers, biopolymers, ligands, ligand receptors, target molecules, nucleotide 5'-α- boranotriphosphates, boron-labels, boron-markers, boron-building-blocks, labeled probes, detection agents, detectable products, preliminary oxidizing agents, and all of the above products attached to solid substrates. In addition these kits contain products including but not limited to distilled water, salts, anti-oxidants, buffers with and without preservatives, solid substrates; and all necessary reagents to carry out the invention including developers, reagents to augment the signal of a detectable product, and reagents to remove excess reactants added to or formed during the steps of the methods described herein.

In one embodiment, a kit for detecting a target molecule comprises two containers. The first container comprises a labeled probe that, when mixed and incubated with a target molecule becomes associated with the target molecule. The second container comprises at least one detection agent that, when combined with the contents of the first container and the target molecule for a sufficient incubation time, yields a detectable product.

In a preferred embodiment, the kit further comprises a third container which contains at least one standard target molecule. A standard target molecule is included to allow the user of the kit to confirm that the kit is working properly.

In a more preferred embodiment the kit, further comprises a fourth container that comprises a developer solution that augments the signal due to the detectable product. In the most preferred embodiment the kit further comprises instructions and protocols for using the kit to detect a target molecule.

Kits can be used to detect target molecules including, but not limited to, peptides, RNA oligomers and DNA oligomers, biooligomers and biopolymers, which include but are not limited to proteins, DNA polymers and RNA polymers.

Another kit embodiment, is a kit for detecting a target molecule, when the target molecule is a DNA oligomer or polymer, or an RNA oligomer or polymer. The kit comprises a 5'-α-boranotriphosphate and reagents to amplify the target molecule. The reagents also incorporate the 5'-α-boranotriphosphate into the target molecule during the amplification of the target molecule. In addition the kit can comprise DNA or RNA oligomers attached to solid substrates. The solid substrates can be any of those described herein. The DNA or RNA oligomers or polymers are complementary to the target molecule.

The kit can also include reagents for washing off unassociated nucleotides and unassociated target molecules from the solid substrate. In addition, the kit can contain a detection agent. The kit can also include reagents for generating a signal after reduction of the detection agent. This reduction of the detection agent is performed by a boron-label that became part of the target molecule as a result of the incorporation of a 5'α-boranonucleotide during the amplification step.

In a preferred embodiment the kit also includes reagents to eliminate unreacted detection agent. It can also include a developer, reagents for augmenting the signal using that developer and reagents for eliminating unreacted developer. In a more preferred embodiment the kit further comprises instructions and protocols for using the kit to detect the target molecule.

An alternative embodiment is a kit for detecting a target molecule attached to a solid substrate. The kit includes reagents to amplify a target molecule and to incorporate a ligand. The kit also includes a labeled probe to bind the target molecule attached to a solid substrate. In addition, the kit can include a detection agent and/or reagents for generating a signal after reduction of the detection agent by the labeled probe and/or reagents to eliminate unreacted detection agent. The kit can also include a developer, and/or reagents for augmenting the signal using the developer and/or reagents for eliminating unreacted developer.

In a preferred embodiment both the target molecule and the labeled probe are DNA or RNA oligomers or polymers. The kit can also include a ligand receptor attached to solid substrate, and/or reagents for washing unassociated nucleotides and unassociated target molecules away from the solid substrate and/or reagents to remove unhybridized labeled probe.

In a more preferred embodiment the kit further comprises a primer containing a nucleotide covalently linked to a ligand, thereby allowing the ligand to be incorporated into the target molecule during amplification. The ligand has a selective affinity for a ligand receptor that is attached to a solid substrate.

In an even more preferred embodiment the kit comprises instructions and protocols for using the kit to detect a target molecule. In the most preferred embodiment the ligand is biotin, and the ligand receptor is either streptavidin or avidin.

The invention also includes a kit for detecting a target molecule that includes a peptide or a protein that contains a boron-label. The peptide or protein in the kit has selective affinity for the target molecule. The kit also includes at least one detection agent that, when combined with the boron labeled peptide or protein produces a detectable product. In a preferred embodiment, the kit includes reagents for generating a signal after reduction of the detection agent by the boron-label and/or reagents to eliminate unreacted detection agent. In a more preferred embodiment, the kit includes a developer, and/or reagents for augmenting the signal using the developer and/or reagents for eliminating unreacted developer. In the most preferred embodiment, the kit further comprises instructions and protocols for detecting a target molecule using the kit.

The detailed description of the invention, described below, will aid in the overall understanding of the invention. However, one skilled in the art will immediately realize that the methods, results and examples presented only help illustrate how the invention works and are not meant to limit the scope of the invention as defined by the appended claims.

"TpT%"=Thymidylyl (3'→5') Thymidine

"TpBT"=Thymidylyl (3'→5') Thymidine Boranephosphonate.

Figures 5A, 5B:
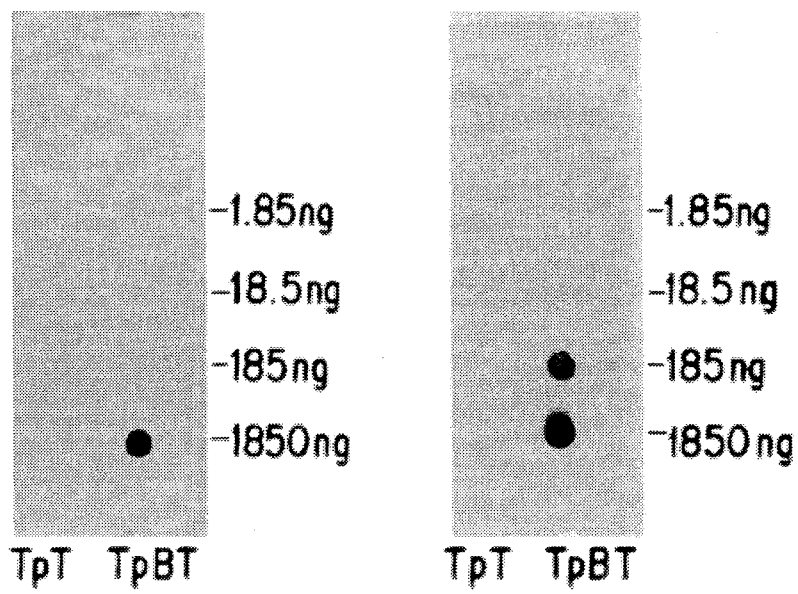

FIG. 5 depicts a silver-stained thin layer chromatography plate of TpT and TpBT obtained by the technique described in Example 5. FIG. 5a shows a thin layer chromatography plate of 1.85 ng, 18.5 ng, 185 ng, and 1850 ng of TpT, and 1.85 ng, 18.5 ng, 185 ng, and 1850 ng of TpBT spotted individually prior to the development step. Only the 1850 ng TpBT spot is visible. FIG. 5b shows the thin layer chromatography plate after the development step. The spots corresponding to 1850 ng and 185 ng of TpBT are plainly visible. Whereas the spot for 18.5 ng of TpBT also is faintly stained and visible in the original photograph, all of the spots corresponding to TpT are not visible.

Figure 6:
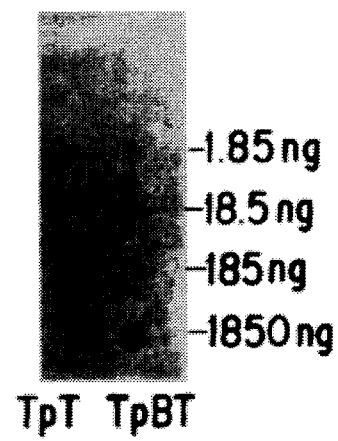

FIG. 6 depicts a palladium-stained nylon membrane of TpT and TpBT solutions pipetted as described in Example 8, using 1.85 ng, 18.5 ng, 185 ng, and 1850 ng of TpT, and 1.85 ng, 18.5 ng, 185 ng, and 1850 ng of TpBT. Once the spots dried, the membrane shown was treated for 1–2 minutes with 0.25% $PdCl_2$. Whereas the spot corresponding to 1850 ng of TpBT spot turned gray, all other spots remained colorless.

Figure 7:
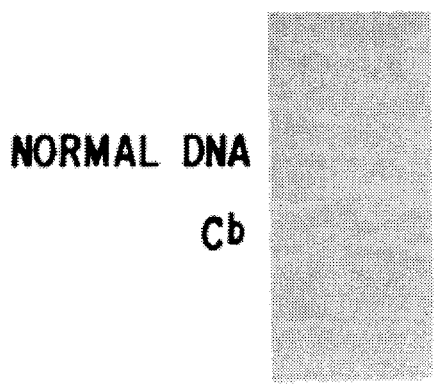

FIG. 7 depicts a palladium stained thin layer chromatography plate showing the stained spot due to 20 μg of $C^bDNA$ and the lack of a stained spot for 20 μg of normal DNA as described in Example 9.

DETAILED DESCRIPTION OF THE INVENTION

Boranotriphosphates

In accordance with the present invention as it applies to the detection of nucleic acids, a preferred embodiment employs nucleoside-α-boranotriphosphates. Nucleoside-α-boranotriphosphates are a relatively new class of nucleic acid derivatives that are analogues of nucleoside-triphosphates and nucleoside-α-thiotriphosphates. (Tomasz et al., *Angew. Chemie. Int. Ed.* (1992), 31, 1373; Porter et al., op. cit.

Deoxynucleoside 5'-α-boranotriphosphates synthesized by the methods described in Tomasz et al. (1992) op. cit., are substrates for a number of polymerases including Klenow, Taq, and vent. However, the boranophosphodiester backbone that is produced upon incorporation of nucleoside-α-boranophosphates into oligonucleotides and polynucleotides is resistant to nuclease activity.

The method of making boronated oligoribonucleosides and deoxyribonucleosides and salts has been described in Schinazi et al., Org. Chem, (1993) 58, 6531 and U.S. Pat. Nos. 5,143,907; 5,177,198; 5,260,427; 5,272,250; which are hereby incorporated by reference.

Peptides containing the boron hydride moiety can be synthesized by the methods described in U.S. Pat. No. 4,977,268 which is hereby incorporated by reference. A method of synthesis also is described by Sood et al., *European J. Med. Chem.* (1990), 25, 301, and by Kane et al., *J. Organic Chem.* (1993), 58, 991. Alternatively, a borane or boron hydride moiety may be attached to a biopolymer by the methods described by Soloway et al., *J. Med. Chem.*, (1989), 32, 2326, Varadarajan et al., *Bioconjugate Chem.* (1991), 2, 242, and Barth et al., in "Progress in Neutron Capture Therapy for Cancer," B. Allen, D. Moore, and B. Harrington, eds., Plenum Press, New York City (1992), p.265.

Oligonucleotides and oligodeoxynucleotides containing a boronated internucleotide phosphodiester linkage represent an important advance in synthetic oligonucleotide technology. The $BH_3^-$ moiety is much more hydrophobic than an 0' moiety and imparts greater membrane permeability than the naturally occurring phosphate group. Furthermore, oligomers or polymers containing boranated nucleotides are much more resistant to nuclease activity. Finally, whereas most compounds containing boron-hydrogen bonds are susceptible to hydrolysis, the borohydride bond in boranophosphates possesses unusual hydrolytic stability.

Figure 1:
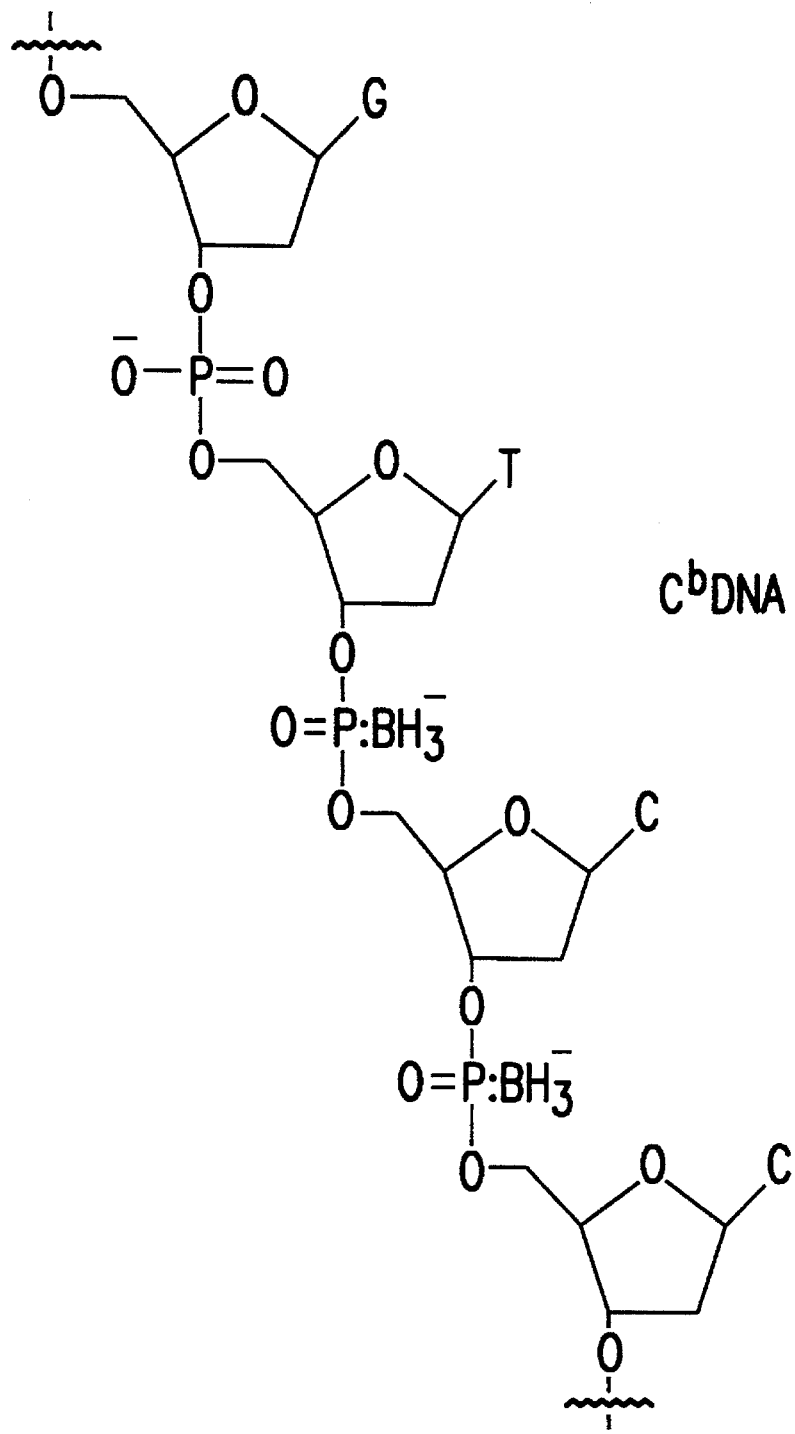
FIG. 1 is the chemical structure of $C^bDNA$. See Definitions.
Figure 2:
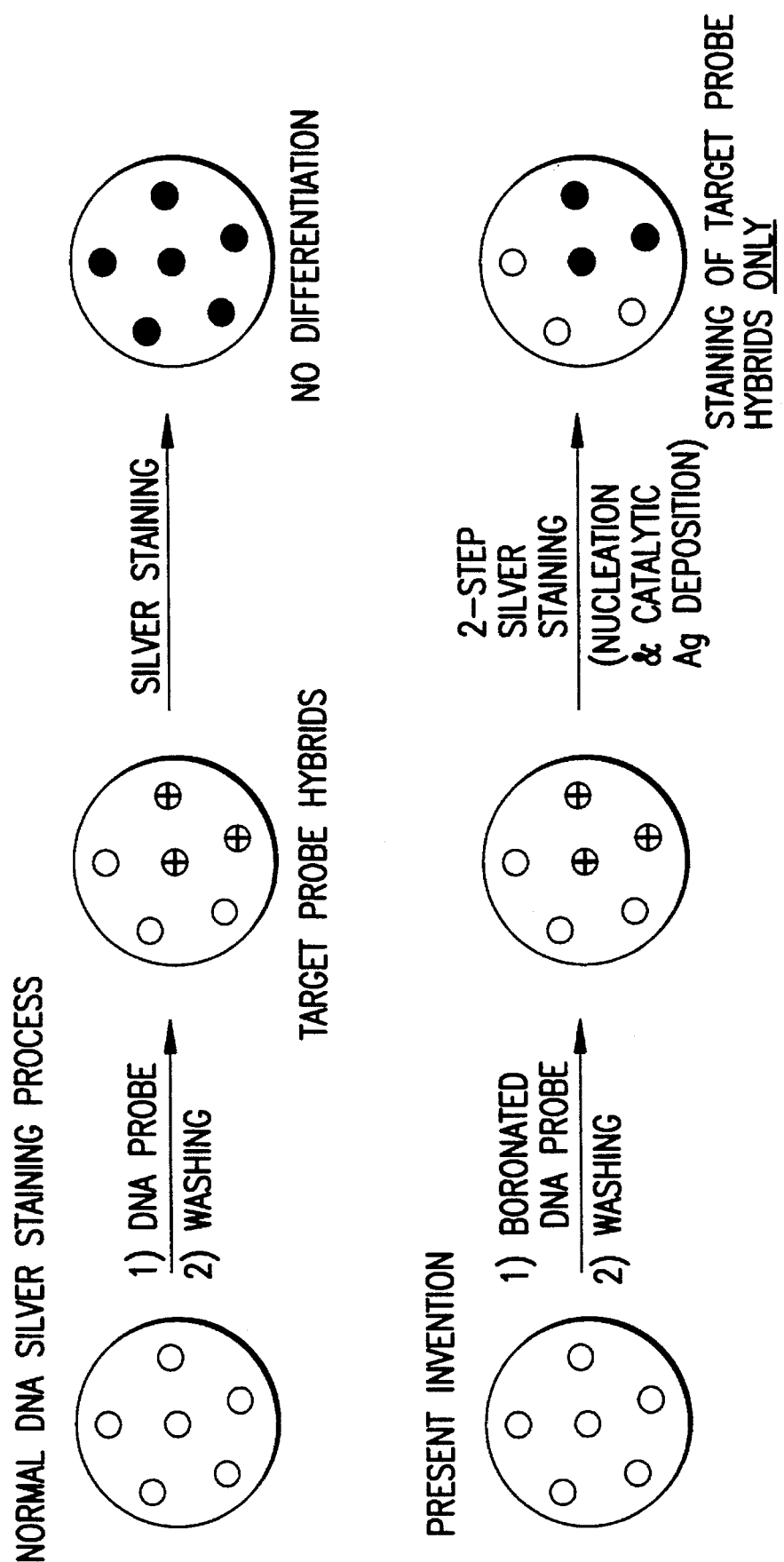
FIG. 2 is a diagram that compares the standard silver staining of DNA with the method of the present invention. In the standard silver staining process all of the DNA is stained, whereas in the present invention only the specific DNA that hybridizes with the labeled probe, i.e., a DNA probe containing a boron-label, is stained.
Figure 3:
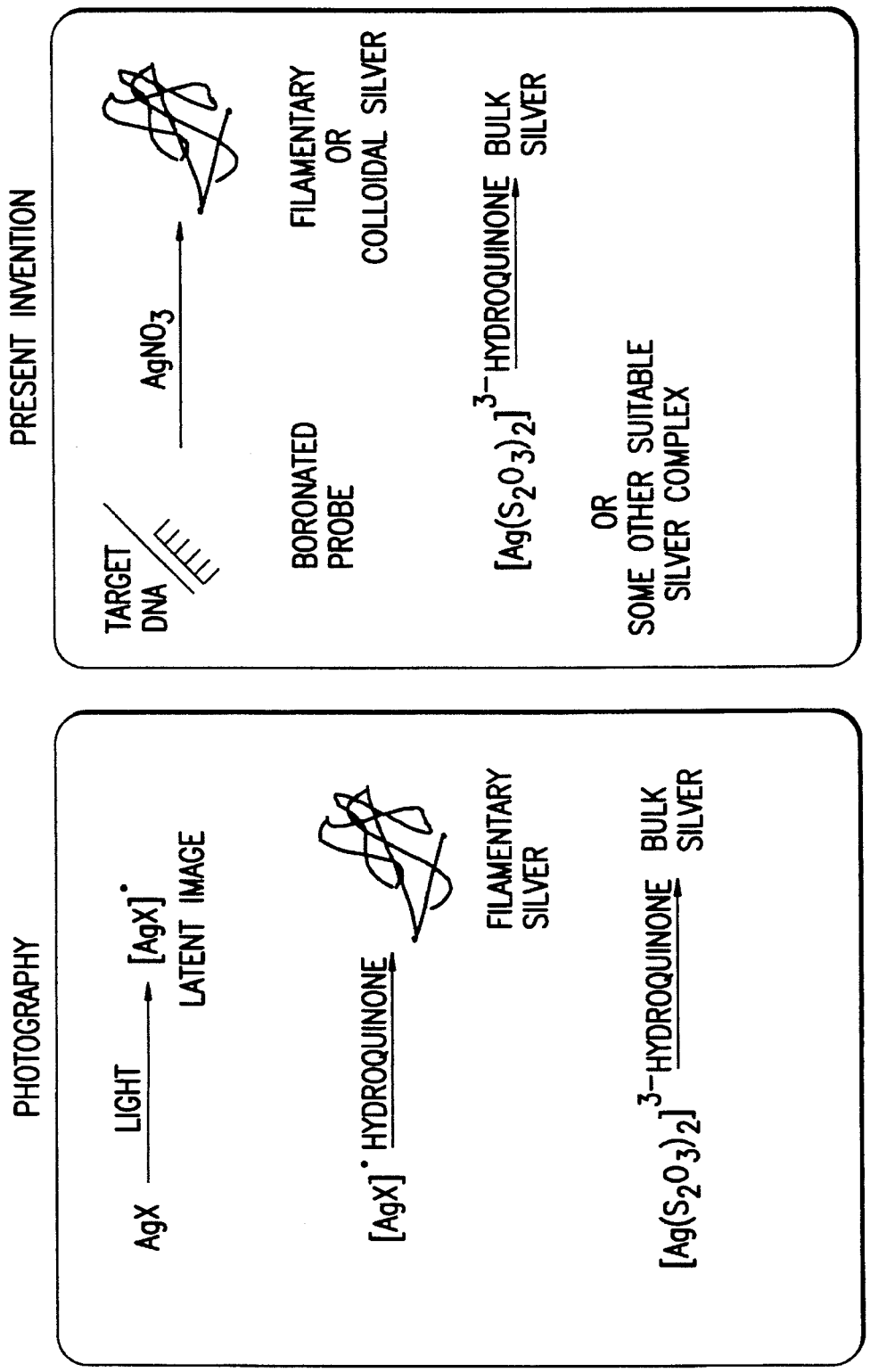
FIG. 3 is a diagram showing the similarities between photography and the present invention when the electron acceptor is silver.

The present invention takes advantage of our observation that boranophosphate oligonucleotides provide a unique opportunity to selectively deposit a large number of metal atoms e.g., silver, at the desired sites for nucleation. According to Hamilton and Urbach, as little as two silver atoms, but generally between 3 to 6 atoms, are sufficient to develop an image in photography. *The Theory of the Photographic Process,* III edition, James, ed., The Macmillan Co., New York City (1966), p.102. One ng of a boronated DNA labeled probes can cause trillions of atoms of silver to be deposited in a square millimeter during the nucleation step. A comparison of the process in photography and the embodiment of the present invention for DNA staining is shown in FIG. 3.

By staining boronated TpT dimer with boranophosphate backbone (185 ng spread over an area of ~5 $mm^2$ on a thin-layer-chromatography plate to obtain a visible stain) we have found that nucleation does occur. In the case where there is one borane group per nucleotide in the DNA labeled probe, this preliminary reduction or nucleation step should be sufficient for visual detection of a bound DNA labeled probe at a concentration of 10 $ng/mm^2$. The amount of target DNA detected depends on the length of the sequence, number of copies of the target sequence, and the total length of target DNA. For example, a target sequence of 200 bases with a copy number of 10 should be detectable at a labeled probe concentration of 100 $ng/mm^2$ (without any amplification of the target molecule) when the total length of the DNA containing the target sequence is 20,000 bases.

In accordance with a preferred embodiment of the present invention, further enhancement of the detectable signal is accomplished by catalytic deposition of silver, permitting detection of considerably lower levels of DNA. As in photography, a few atoms can be "developed" to a micron-size silver particle. Therefore, detectability of DNA using this technique is theoretically more sensitive than even chemiluminescence. However, in practice, due to potential background staining (which should be lower in this case than in regular silver staining due to selective nucleation) it may be similar to chemiluminescence. A detection limit for DNA of 5–7.5 $pg/mm^2$ has been reported using conventional silver staining, (Beidler, et al., *Analytical Biochemistry* (1982), 126, 374.

Large fragments of boronated DNA (678 basepairs) containing approximately 25% boranophosphate linkages can be readily stained using normal methods e.g. using a silver sequence DNA sequencing kit supplied by Promega of Madison, Wis., catalog #Q4132. The stain appears more intense than that for the regular DNA. Boronated TpT nucleotide dimers will catalyze nucleation with $AgNO_3$ in the absence of any other reducing agent, whereas normal TpT dimers cannot be detected.

Incorporation of the boron hydrogen moiety into a nucleic acid labeled probe results in the production of a hydrolytically stable nucleic acid labeled probe that contains a powerful reducing label. It is well known in boron hydride chemistry that the B-H bond is reactive with a number of metal cations, producing either the free metal or metal boride. Additionally, the reducing action of B-H can also produce colored species, e.g. $W^{6+}$ can be reduced to tungsten blue.

Metals reduced by sodium borohydride include cadmium, cobalt, copper, gold, iridium, lead, mercury, nickel, palladium, platinum, rhenium and silver. Complexes containing BH such as an amine or a phosphite can also reduce many of the aforesaid metals.

Palladium, $Pd^{2+}$, is extremely susceptible to reduction by BH, yielding palladium metal. In accordance with an alternative embodiment of the present invention, the palladium metal resulting therefrom acts as a nucleus for the development of a signal using salts of metals such as gold, nickel, cobalt, and copper by the methods described in U.S. Pat. No. 3,937,857, the subject matter of which is hereby incorporated by reference.

Nucleotide labeled probes

One major advantage of nucleic acid labeled probes containing borohydride moieties is the ability of these labeled probes to selectively deposit highly catalytic metals such as palladium, upon which further depositions of metals such as nickel, cobalt, copper, gold, etc. can be carried out. Although relatively expensive palladium salts may be necessary, the amount utilized is extremely small and the signal augmentation can be carried out using less expensive and/or less toxic metal cations such as nickel, cobalt and copper ions.

Quantitation using conventional silver staining methods is not as straightforward as with many other detection systems. The main reason for this is the fact that after initial nucleation, the process for further deposition of silver is catalytic. Since with prior silver staining methods, the initial nucleation is not controlled, it is difficult to quantify the overall silver deposition. Even with the problems, it has been possible to quantify silver staining. For example, for protein staining silver deposition is linear over a wide range 0.05 ng $-2$ ng/mm$^2$. For DNA staining the range has been reported to be 25–250 ng for short DNA and 0.25–4 ng for DNA that has at least 271 base pairs.

In the present invention, the initial nucleation step may be controlled to deposit six silver atoms per borano-phosphate group. The nucleation should not be dependent on DNA length or base composition. In contrast, with prior silver staining techniques, there have been reports of stronger stains with shorter oligonucleotides as compared to longer nucleotides. After nucleation, the rate of deposition is mainly governed by the properties of the developing solution and the catalytic activity of the nucleation centers. Therefore, silver staining with boronated oligonucleotides should be linear over a larger range of DNA concentration than with prior techniques, so it may be more easily quantified than with prior techniques.

Biotinylated nucleotides are available from CLONTECH Laboratories, Inc. Palo Alto, Calif. All other reagents described herein, other than the boron labeled nucleotides, are available from Aldrich Chemical Company of Milwaukee, Wis., Sigma Chemical Company, St. Louis, Mo. or other similar suppliers of chemicals that would be are known to those skilled in the art.

EXAMPLES

Example 1

One-µl aliquots of either 2 mM TpT or 2 mM TpBT were spotted individually onto a silica gel thin layer chromatography plate. After the spots were dry, the plate was sprayed with 2% aqueous silver nitrate. The TpBT spot turned brown whereas the TpT spot remained colorless.

The thin layer chromatography plate was next placed in the developer described below for 16 minutes. The TpBT spot transformed to a dark blue spot with a black outer ring whereas the TpT spot remained undetectable.

The developer was prepared by mixing Solution A with Solution B:

Solution A: 100 mg silver acetate in 40 ml $H_2O$;
Solution B: 200 mg of hydroquinone in 40 ml of citrate buffer, pH=3.8 (2.35 g of trisodium citrate dihydrate and 2.55 g of citric acid in 85 ml
of deionized water—pH was adjusted with citric acid)

Example 2

One µl each of 20 µM, 0.2 mM, and 2 mM TpT, and 20 µM, 0.2 mM and 2 mM TpBT were spotted individually onto a silica gel thin layer chromatography plate and the spots were allowed to dry. Then the plate was sprayed with 2% aqueous $AgNO_3$ solution and allowed to dry at room temperature. The spot of 2 mM TpBT turned light brown. All other spots remained colorless. The plate was then placed for ten minutes into an oven that had been preheated to 90° C. (±10° C.). The spot of 2 mM TpBT turned dark brown and that of 0.2 mM TpBT turned light brown. All other spots, including that of 20 µM TpBT, remained colorless. Placing the plate in the developer for 15 minutes resulted in no additional spots staining, and no change in the staining of the visible spots.

Example 3

One µl each of 20 µM, 0.2 mM, and 2 mM TpT, and 20 µM, 0.2 mM and 2 mM TpBT were spotted individually onto a silica gel thin layer chromatography plate and the spots were allowed to dry. Next the plate was sprayed with $AgNO_3$ (in about a 2% aqueous solution) and then dried with a stream of warm air. The spots corresponding to 2 mM and 0.2 mM TpBT stained. All the other spots remained unstained.

The plate was next placed for seven minutes in a developer made by mixing solution A with solution B:
Solution A: 100 mg silver lactate in 40 ml $H_2O$;
Solution B: 200 mg hydroquinone in 40 ml citrate buffer, pH=3.8 (prepared as described in Example 1).

Whereas all of the spots of TpBT were now detectable, all of the spots of TpT remained indistinguishable from the gray background of the plate.

Example 4

One µl each of 2 µl, 20 µM, 0.2 mM, and 2 mM TpT, and 2 µl, 20 µM, 0.2 mM and 2 mM TpBT were spotted individually onto a silica gel thin layer chromatography plate and the spots were allowed to dry. Next the plate was dipped for thirty seconds into a solution of about 0.25% $PdCl_2$ in 1% HCl.

Figure 4:
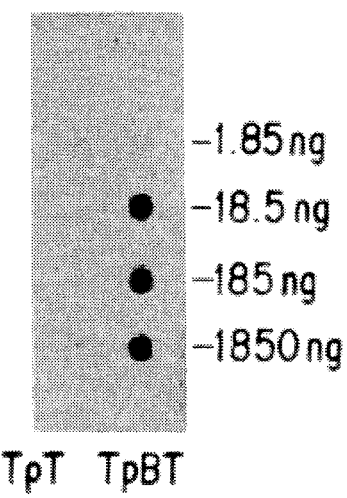
FIG. 4 depicts a palladium-stained thin layer chromatography plate containing individual spots of 1.85 ng, 18.5 ng, 185 ng, and 1850 ng of TpT, and 1.85 ng, 18.5 ng, 185 ng, and 1850 ng of TpBT, prepared by the technique described in Example 4. Whereas, the spots containing 18.5 ng, 185 ng, and 1850 ng TpBT are visible, the spot containing 1.85 ng of TpBT, and all spots containing TpT are not. The background of the plate is gray.

Whereas, the spots for the three higher concentrations of TpBT were now detectable, all of the spots of TpT remained indistinguishable from the gray background of the plate. See FIG. 4.

Example 5

One µl each of 2 µM, 20 µM, 0.2 mM, and 2 mM TpT, and 2 µM, 20 µM, 0.2 mM, and 2 mM TpBT were spotted individually onto a silica gel thin layer chromatography plate and the spots were allowed to dry. Next the plate was placed for fifteen minutes into an aqueous 1% $AgNO_3$ solution. Only the 2 mM TpBT spot stained.

The plate was then placed for about fifteen minutes into a developer chamber containing 25 ml of solution A and 50 ml of solution B (light-stable developer as described by U.S. Pat. No. 5,206,122 which is hereby incorporated by reference).

| Solution A: | Solution B: |
|---|---|
| 1.785 g citric acid | 3.29 g sodium citrate |
| 0.705 g sodium citrate | 1.0 g sodium sulfite |
| 4.0 g imidazole | 0.06 g hydroquinone |
| 0.186 g AgNO$_3$ | 1.532 g citric acid in 100 ml H$_2$O |
| 50 ml H$_2$O | |

The spots corresponding to 0.2 mM and 2 mM TpBT clearly stained whereas the 20 µM spot of TpBT only lightly stained. All of the TpT spots remained colorless. See FIG. 5.

Example 6

Two aluminum-backed silica gel thin layer chromatography plates were spotted with one µl each of 0.2 mM, 20 µM and 2 µM TpT and 0.2 mM, 20 µM and 2 µM TpBT solutions and the spots were allowed to dry. Next the plates were placed, individually for about fifteen minutes, into a 1% aqueous AgNO$_3$ solution.

The plates were then placed into a light stable developer prepared as described in U.S. Pat. No. 5,206,122 (for protected physical developer I) from solution A and solution B.

| Solution A: | Solution B: |
|---|---|
| 1.785 g citric acid | 3.29 g sodium citrate |
| 0.705 g sodium citrate | 1.0 g sodium sulfite |
| 4.0 g imidazole | 0.060 mg N(p-hydroxyphenyl) glycine |
| 0.186 g silver nitrate | 1.532 g citric acid and 100 ml H$_2$O |
| 50 ml H$_2$O. | |

Two developers were prepared:
1. 40 ml of solution B was added to 20 ml of solution A, and
2. 30 ml of solution B was added to 30 ml of solution A.

One plate was placed for approximately 15 minutes into each developer. The spots corresponding to 0.2 mM and 20 µM TpBT were stained on both plates. Whereas the spot of 2 µM TpBT stained lightly, all of the spots of TpT remained colorless.

Example 7

A silica gel thin layer chromatography plate was spotted with one µl of 2 mM, 0.2 mM and 20 µM boronated glycylglycine amide (NH$_3$BH$_2$CONHCH$_2$CONH$_2$) and allowed to dry. Next the plate was placed for fifteen minutes into a chamber filled with 1% aqueous silver nitrate. The 2 mM boronated peptide spot stained brown whereas the 0.2 mM spot was only lightly stained.

The plate was then immersed in developer 2 as described in Example 6, for 10 minutes. The staining of the 2 mM and 0.2 mM boronated peptide spots were enhanced. The boronated peptide spot at 20 µM remained colorless.

Example 8

One µl each of 2 µM, 20 µM, 0.2 mM, and 2 mM TpT, and 2 µM, 20 µM, 0.2 mM and 2 mM TpBT individually were pipetted onto two nylon membranes and the spots were allowed to dry. Next, one membrane was placed for thirty minutes into an aqueous solution of 1% AgNO$_3$ and then for fifteen minutes in the developer described in Example 5. The 2 mM TpBT spot stained, appearing as a light yellow spot. The other membrane was treated for 1–2 minutes with 0.25% PdCl$_2$. Whereas the 2 mM TpBT spot turned gray, all other spots remained colorless. See FIG. 6.

Example 9

A glass-backed silica gel thin layer chromatography plate was spotted with 20 µg (10 µl of 2 µg/µl solution) of normal DNA and 20 µg of C$^b$DNA and the spots were allowed to dry. Next the plate was dipped into a solution of 0.25% PdCl$_2$ in 1% HCl for about 10 minutes. The thin layer plate had light staining for the spot corresponding to C$^b$DNA, but no staining for the normal DNA. See FIG. 7.

It should be understood that the examples presented above are merely for purposes of illustration.

We claim:

1. A method for detecting a target molecule, wherein said method comprises the steps of:

(a) contacting a target molecule with an unassociated boron-marker, thereby forming an associated boron-marker;

(b) eliminating remaining unassociated boron-marker;

(c) adding to said associated boron-marker, a detection agent capable of being chemically reduced by said associated boron-marker, thereby forming a detectable product which produces a signal;

(d) incubating said associated boron-marker and said detection agent so as to chemically reduce said detection agent and form a detectable product; and (e) detecting the detectable product, wherein the signal is detected by visual detection or with the aid of analytical equipment, whereby the target molecule is detected; and wherein, "target molecule" is the generic term for molecules that are selected to be detected;

a "ligand" is an organic or inorganic molecule that binds, with selective affinity, to a ligand receptor;

a "ligand receptor" is an organic or inorganic molecule or polymer which binds with selective affinity to a ligand;

a "boron-label" is a borane or boron hydride moiety capable of reducing a detection agent, resulting in the formation of one or more detectable products;

a "boron-building-block" is a small organic molecule that comprises one or more boron-labels, and can sere as the repeat unit of a biopolymer or a biooligomer;

a "labeled probe" is a biopolymer, biooligomer, ligand receptor, or ligand, that comprises at least one boron-label and has a selective affinity to associate with a target molecule such that, when associated with the appropriate target molecule, the target molecule can be detected;

a "boron-marker" is a boron-label, a boron-building-block, and/or a labeled probe that is capable of being associated with a target molecule;

an "associated boron-marker" is a boron-marker bound to a target molecule by means including but not limited to covalent bonds, and/or hydrogen bonds, and/or ionic interactions, and/or hydrophobic interactions, and/or charge-transfer complexation, and/or metal to ligand coordination bonds;

an "unassociated boron-marker" is a boron-marker that is not associated with a target molecule;

a "bioorganic polymer" is a polymer comprising nucleotides, amino acids, sugars, or combinations thereof;

a "biooligomer" is a bioorganic polymer comprising at least two but not more than 50 nucleotides, amino acids, sugars, or combinations thereof;

a "biopolymer" is an bioorganic polymer comprising 51 or more nucleotides, amino acids, sugars, or combinations thereof;

a "detection agent" is either an organic or inorganic electron acceptor that is capable of being reduced by a boron-label to form a detectable product;

a "detectable product" is a product of the reaction of a boron-marker, defined below, with a detection agent, said product alone or through an additional chemical development step produces (and/or augments) a signal that can be detected by one or more means; and a "signal" is that property produced by the detectable product that is detectable.

2. The method of claim 1 wherein said incubating of said associated boron-marker and said detection agent in step (d) comprises an incubation period of 1 to 30 minutes, at 15°–30° C., and at pH 3–8.

3. The method of claim 2, wherein the detection agent is an organic dye in the oxidized state.

4. The method of claim 2, wherein the detection agent is a metal salt or complex, that upon reduction is either reduced to its metallic state, forms a metal boride, or forms a colored metal oxide.

5. The method of claim 4, wherein said metal salt or complex is selected from the group consisting of silver, cadmium, cobalt, copper, gold, iridium, lead, mercury, nickel, palladium, platinum, and rhenium salts or complexes.

6. The method of claim 5, wherein the detection agent is a silver salt or complex.

7. The method of claim 4, wherein an excess of detection agent is added in step (c) and the detectable product serves as a nucleation site for further development of the signal through the reduction of the additional detection agent during step (d).

8. The method of claim 4, wherein the metal of the metal salt or complex of the detection agent added in step (c) is selected from the group consisting of palladium and platinum, at valence state +2;

further comprising a step for adding a second metal contained in a metal salt or metal complex selected from the group consisting of nickel, copper, cobalt, silver, and gold salts or complexes; and wherein the palladium or platinum reduced by the boron-marker serves as a nucleation site for the electroless plating of said second metal, thereby initiating further development of the signal.

9. The method of claim 7, wherein said boron-marker is a labeled probe.

10. The method of claim 1, wherein said boron-marker is a labeled probe.

11. The method of claim 10, wherein said labeled probe is selected from the group consisting of biopolymers and biooligomers.

12. The method of claim 11, wherein both the target molecule and the labeled probe are selected from the group consisting of RNA polymers, DNA polymers, RNA oligomers, and DNA oligomers; and wherein, a "nucleotide" is selected from the group consisting of a small organic molecule composed of an N-glycoside of a heterocyclic base, in which the glycoside is also in an ester linkage with a phosphate, and modifications and derivatives thereof;

an "RNA nucleotide" is a nucleotide, wherein the sugar moiety of the glycoside in the nucleotide is ribose;

a "DNA nucleotide" is a nucleotide, wherein the sugar moiety of the glycoside in the nucleotide is deoxyribose;

an "RNA oligomer" is a biooligomer comprising at least two but not more than 50 RNA nucleotides;

a "DNA oligomer" is a biooligomer comprising at least two but not more than 50 DNA nucleotides;

an "RNA polymer" is a biopolymer comprising 51 or more RNA nucleotides; and a "DNA polymer" is a biopolymer comprising 51 or more DNA nucleotides.

13. The method of claim 11, wherein said labeled probe is selected from the group consisting of proteins and peptides; and wherein, a "protein" is a biopolymer comprising 51 or more amino acids; and a "peptide" is a biooligomer comprising two but not more than 50 amino acids.

14. The method of claim 13, wherein said labeled probe is a protein selected from the group consisting of antibodies and lectins.

15. The method of claim 10, further comprising the step of attaching said target molecule to a solid substrate.

16. The method of claim 15, wherein the solid substrate is selected from the group consisting of a membrane, a microtiter plate and beads.

17. The method of claim 10, wherein step (b) is performed by adding a preliminary oxidizing agent to selectively oxidize the boron-label of the unassociated labeled probe prior to the addition of the detection agent; wherein a preliminary oxidizing agent is an oxidizing agent that when added to a mixture of associated boron-marker and unassociated boron-marker, selectively oxidizes the boron-label comprised by the unassociated boron-marker.

18. The method of claim 17, wherein said preliminary oxidizing agent is attached to a solid substrate.

19. The method of claim 1, wherein said boron-marker is a boron-building-block; and wherein contacting a target molecule with the unassociated boron-marker in step (a) comprises synthesizing said target molecule in the presence of said boron-marker so as to incorporate said boron-marker into said target molecule.

20. The method of claim 19, wherein an excess of detection agent is added in step (c) and the detectable product serves as a nucleation site for further development of the signal through the reduction of the additional detection agent during step (d).

21. The method of claim 19, wherein the metal of the metal salt or complex of the detection agent added in step (c) is selected from the group consisting of palladium and platinum, at valence state +2;

further comprising a step for adding a second metal contained in a metal salt or metal complex selected from the group consisting of nickel, copper, cobalt, silver, and gold salts or complexes; and wherein the palladium or platinum reduced by the boron-marker serves as a nucleation site for the electroless plating of said second metal, thereby initiating further development of the signal.

22. The method of claim 19, wherein said target molecule is selected from the group consisting of RNA polymers, RNA oligomers, DNA polymers, and DNA oligomers.

23. The method of claim 19, wherein said target molecule is selected from the group consisting of proteins and peptides.

24. A method of detecting DNA oligomers or polymers during the sequencing of DNA polymers and oligomers comprising the steps of:

(a) placing deoxyadenosine 5'-α-boranotriphosphate, deoxythymidine 5'-α-boranotriphosphate, deoxycytosine 5'-α-boranotriphosphate, and deoxyguanosine 5'-α-boranotriphosphate into four separate polymerase chain reaction amplification containers, each container also containing standard deoxynucleoside triphosphates, wherein the standard deoxynucleoside triphosphates are deoxyadenosine triphosphate, deoxythymidine triphosphate, deoxycytosine triphosphate, and deoxyguanosine triphosphate;

(b) adding primers and template and performing polymerase chain reaction amplifications;

(c) synthesizing polymerase chain reaction amplification products containing boranomonophosphate linkages;

(d) adding an exonuclease to truncate said polymerase chain reaction amplification products, whereby the resulting oligomers or polymers terminate at a boranomonophosphate linkage;

(e) separating said resulting borano-terminated oligomers or polymers;

(f) adding to said separated borano-terminated oligomers or polymers, a detection agent capable of being chemically reduced by said borano-terminated oligomers or polymers to form a detectable product;

(g) incubating said borano-terminated oligomers for polymers and said detection agent so as to chemically reduce said detection agent, whereby said detectable product is produced; and (h) detecting the signal produced by the detectable product by visual detection or with the aid of analytical equipment, whereby the DNA oligomers or polymers are detected; wherein a boranomonophosphate is a nucleoside monophosphate wherein the phosphate group of the nucleotide has a —$BH_3$ moiety in place of a non-bridging oxygen;

a boranomonophosphate linkage is a linkage between two nucleotides wherein the two nucleotides are linked via a phosphate linkage having a —$BH_3$ moiety in place of a non-bridging oxygen; and a borano-terminated oligomer or polymer is an oligomer or polymer of an RNA or DNA polymer or oligomer that has been at least partially digested by a nuclease, and wherein the terminal nucleotide linkage of the oligomer or polymer has a —$BH_3$ moiety in place of a non-bridging oxygen.

25. The method of claim 24 wherein said incubating of said associated boron-marker and said detection agent in step (g) comprises an incubation period of 1 to 30 minutes, at 15°–30° C., and at pH 3–8.

26. The method of claim 25, wherein the separation of said borano-terminated oligomers or polymers is achieved by electrophoresis, and wherein said detection agent is a metal salt or metal complex.

27. The method of claim 26, wherein the metal salt or complex used comprises either silver, platinum, or palladium.

28. The method of claim 27 wherein an excess of detection agent is added in step (f) and the detectable product serves as a nucleation site for further development of the signal through the reduction of the additional detection agent during step (g).

29. A method for detecting a target molecule, comprising the steps of:

(a) hybridizing a labeled probe with a target molecule, wherein said target molecule comprises a nucleic acid;

(b) eliminating remaining unhybridized labeled probe;

(c) adding to said hybridized labeled probe, a detection agent selected from the group consisting of a soluble silver salt and a silver complex;

(d) incubating said hybridized labeled probe with said detection agent under conditions and for a time sufficient to chemically reduce the silver ion to its metallic state;

(e) catalytically depositing more silver using a silver developer; and (f) detecting the metallic silver, wherein the silver is detected by visual detection or with the aid of analytical equipment, Whereby the target molecule is detected.

30. A method of detecting a target molecule, comprising the steps of:

(a) amplifying a target molecule, wherein said target molecule comprises a nucleic acid, wherein said amplification is performed with nucleotides selected from the group consisting of 5'-α-boranotriphosphates, and 5'-α-boranotriphosphates mixed with standard nucleoside triphosphates, and wherein said amplification is achieved by a process selected from the group consisting of polymerase chain reaction, in situ polymerase chain reaction, strand displacement amplification, self-sustained sequence replication, replication using Qβ replicase, ligase chain reaction, and transcription based amplification;

(b) hybridizing said amplified target molecule to DNA or RNA oligomers or polymers, that are complementary to the target molecule, wherein said oligomers or polymers are attached to a solid substrate;

(c) eliminating unassociated nucleotides and unhybridized target molecules;

(d) adding to said hybridized target molecule, a detection agent;

(e) incubating said hybridized target molecule with said detection agent, so as to chemically reduce said detection agent and form a detectable product which produces a signal;

wherein the detection agent is a metal salt or metal complex, and wherein said detectable product can also serve as a nucleation site for the formation of additional detectable product development, and thereby augment the signal;

(f) eliminating the unreduced detection agent;

(g) augmenting said signal using a developer solution, said developer solution comprising a second detection agent, a reducing agent, and a stabilizer, wherein said second detection agent is selected from the group consisting of a metal complex, a metal salt and an organic dye, and wherein said developer is stable in the absence of the nucleation site produced in step (e);

(h) eliminating remaining developer solution; and (i) detecting the augmented signal by visual detection or with the aid of analytical equipment, whereby the target molecule is detected.

31. The method of claim 30, wherein the elimination of unassociated nucleotides and unhybridized target molecules in step (c);

the elimination of the unreduced detection agent in step (f); and the elimination of the remaining developer solution in step (h) are each accomplished by washing the solid substrate.

32. A method of determining whether a target molecule is contained in a sample comprising the steps of:

(a) amplifying a target molecule in a sample, wherein said target molecule comprises a nucleic acid, wherein said amplification is performed with a primer containing a covalently linked ligand, thereby forming an amplified target molecule covalently linked to said ligand, and performed with either RNA nucleotides or DNA nucleotides but are not 5'-α-boranotriphosphates, and wherein said amplification is achieved by a process selected from the group consisting of polymerase chain reaction, in situ polymerase chain reaction, strand displacement amplification, self-sustained sequences replication, replication using Qβ replicase, ligase chain reaction, and transcription based amplification;

(b) associating said amplified target molecule with a ligand receptor attached to a solid substrate, thereby forming a ligand-ligand receptor complex attached to a solid substrate;

(c) eliminating unassociated nucleotides and unassociated target molecules;

(d) hybridizing said ligand-ligand receptor complex attached to a solid substrate with a labeled probe complementary to the target molecule, forming a hybridized labeled probe, said labeled probe selected from the group consisting of a DNA oligomer and a DNA polymer;

(e) eliminating unhybridized labeled probe;

(f) contacting said hybridized labeled probe with a detection agent capable of being chemically reduced by said hybridized labeled probe;

(g) incubating said hybridized labeled probe and said detection agent so as to chemically reduce said detection agent and form a detectable product which produces a signal, wherein the detection agent is a metal salt or metal complex, and wherein said detectable product also serves as a nucleation site for the formation of additional detectable product development, thereby augmenting the signal;

(h) eliminating the unreduced detection agent;

(i) augmenting said signal using a developer solution, said developer solution comprising a second detection agent, a reducing agent, and a stabilizer, wherein said second detection agent is selected from the group consisting of a metal complex, a metal salt and an organic dye, and wherein said developer is stable in the absence of the nucleation site produced in step (g);

(j) eliminating the remaining developer solution; and (k) detecting the augmented signal by visual detection or with the aid of analytical equipment, whereby the detection of said signal indicates that said target molecule is contained in the sample, wherein a "boron-label" is a borane, or boron hydride moiety; and a "labeled probe" is a biopolymer, biooligomer, ligand receptor, or ligand, that comprises at least one "boron-label" and has a selective affinity to associate with a target molecule such that, when associated with the appropriate target molecule, the target molecule can be detected.

33. The method of claim 32 wherein the ligand is biotin, and wherein the ligand receptor is streptavidin or avidin.

34. The method of claim 32, wherein in step (c) the elimination of unassociated nucleotides and unassociated target molecules;

in step (e) the elimination of unhybridized labeled probe;

in step (h) the elimination of the unreduced detection agent; and in step (j) the elimination of the remaining developer solution are each accomplished by washing them away from the solid substrate.

35. A kit for detecting a target molecule, comprising:

(a) a first, second and third container;

(b) said first container containing at least one standard target molecule;

(c) said second container containing a labeled probe that, when mixed and incubated with the contents of said first container becomes associated with the target molecule, and;

(d) said third container containing at least one detection agent that, when combined with the incubated contents of said first and second containers results in a detectable product which produces a signal;

wherein a "boron-label" is a borane, or boron hydride moiety; and a "labeled probe" is a biopolymer, biooligomer, ligand receptor, or ligand, that comprises at least one "boron-label" and has a selective affinity to associate with a target molecule such that, when associated with the appropriate target molecule, the target molecule can be detected.

36. The kit according to claim 35, wherein said detectable product also serves as a nucleation site for the formation of additional detectable product development; and further comprising a fourth container, said fourth container containing a developer solution that reacts with said nucleation site to augment the signal.

37. The kit according to claim 35 further comprising protocols for using the kit to detect a target molecule.

38. The kit according to claim 35 wherein the target molecule is a biopolymer.

39. A kit for detecting a target molecule, comprising:

(a) a 5'-α-boranotriphosphate;

(b) reagents to amplify a target molecule and incorporate said 5'-α-boranotriphosphate into said target molecule during amplification;

(c) DNA or RNA oligomers or polymers attached to solid substrates, said DNA or RNA oligomers or polymers being complementary to said target molecule;

(d) reagents for washing off unassociated nucleotides and unhybridized target molecules away from said solid substrate;

(e) a detection agent and reagents for generating a signal after reduction of the detection agent by said amplified target molecule;

(f) reagents to eliminate unreduced detection agent;

(g) a developer, and reagents for augmenting the signal using said developer; and (h) reagents for eliminating remaining developer, wherein a "detection agent" is either an organic or inorganic electron acceptor that is capable of being reduced by a boron-label to form a detectable product.

40. The kit according to claim 39 further comprising protocols for using the kit to detect a target molecule.

41. A kit for detecting a target molecule associated with a solid substrate, comprising:

(a) a primer containing a nucleotide covalently linked to a ligand, wherein said ligand is allowed to be incorporated into a target molecule during amplification;

(b) reagents to amplify the target molecule;

(c) a ligand receptor that has selective affinity to said ligand, wherein said ligand receptor is attached to a solid substrate and wherein said target molecule becomes associated with the solid substrate;

(d) reagents for washing unassociated nucleotides and unassociated target molecules away from the solid substrate;

(e) a labeled probe competent to hybridize with the target molecule associated with the solid substrate;

(f) reagents to remove unhybridized labeled probe;

(g) a detection agent and reagents for generating a signal after reduction of the detection agent by the labeled probe;

(h) reagents to eliminate unreduced detection agent;

(i) a developer, and reagents for augmenting the signal using said developer; and (j) reagents for eliminating remaining developer, wherein a "boron-label" is a borane, or boron hydride moiety; and a "labeled probe" is a biopolymer, biooligomer, ligand receptor, or ligand, that comprises at least one "boron-label" and has a selective affinity to associate with a target molecule such that, when associated with the appropriate target molecule, the target molecule can be detected.

42. The kit according to claim 41 further comprising protocols for using the kit to detect a target molecule.

43. A kit for detecting a target molecule comprising a peptide or a protein, said peptide or said protein comprising a borane, or boron hydride moiety, and at least one detection agent that, when combined with the said peptide or said protein produces a detectable product.

44. The kit according to claim 43, wherein said detectable product also serves as a nucleation site for the formation of additional detectable product development; and further comprising a developer solution that reacts with said nucleation site to augment the signal.

45. The kit according to claim 44 further comprising protocols for using the kit to detect a target molecule.

* * * * *